(12) United States Patent
Kato et al.

(10) Patent No.: US 11,560,599 B2
(45) Date of Patent: Jan. 24, 2023

(54) ONION DISCRIMINATION METHOD

(71) Applicant: House Foods Group Inc., Osaka (JP)

(72) Inventors: Masahiro Kato, Higashiosaka (JP); Noriya Masamura, Higashiosaka (JP); Masae Ueyama, Higashiosaka (JP)

(73) Assignee: HOUSE FOODS GROUP INC., Osaka (JP)

( * ) Notice: Subject to any disclaimer, the term of this patent is extended or adjusted under 35 U.S.C. 154(b) by 0 days.

(21) Appl. No.: 16/650,677

(22) PCT Filed: Sep. 21, 2018

(86) PCT No.: PCT/JP2018/035044
§ 371 (c)(1),
(2) Date: Mar. 25, 2020

(87) PCT Pub. No.: WO2019/059350
PCT Pub. Date: Mar. 28, 2019

(65) Prior Publication Data
US 2020/0248276 A1    Aug. 6, 2020

(30) Foreign Application Priority Data

Sep. 25, 2017 (JP) .............................. JP2017-184019

(51) Int. Cl.
| C12Q 1/68 | (2018.01) |
| C12Q 1/6888 | (2018.01) |
| C12Q 1/6844 | (2018.01) |

(52) U.S. Cl.
CPC ......... *C12Q 1/6888* (2013.01); *C12Q 1/6844* (2013.01); *C12Q 2600/16* (2013.01)

(58) Field of Classification Search
None
See application file for complete search history.

(56) References Cited

U.S. PATENT DOCUMENTS

2016/0073607 A1*  3/2016  Kato ...................... C12N 15/01
800/260

FOREIGN PATENT DOCUMENTS

| EP | 2992756 A1 | 3/2016 |
| JP | 5671657 B1 | 2/2015 |
| JP | 56716578 B1 | 2/2015 |
| WO | 2014/178420 A1 | 11/2014 |

OTHER PUBLICATIONS

Lancaster, JE et al. (2000). A novel Alliinase from roots. Biochemical characterization and cDNA cloning. Plant Physiology, vol. 122, p. 1269-1279.*

Endo et al. distinct intraspecific variations of garlic (Allium Sativum L) revealed by the exon-intron sequences of the alliinase gene. J Nat Med., vol. 68, p. 442-447, 2014.*
Van Damme et al. Isolation and characterization of alliinase cDNA clones from garlic (*Alliumn Sativum* L) and related species. Eur. J. Biochem., vol. 209, p. 751-757, 1992.*
Masamura et al. Identification of amino acid residues essential for onion lachrymatory fetor synthase activity. Biosci. Biotechnol. Biochem., vol. 76(3), p. 447-453, 2012.*
Kato et al., Production and characterization of tearless and non-pungent onion, Scientific Reports, 6: 23779 (2016).
King et al., "A low-density genetic map of onion reveals a role for tandem duplication in the evolution of an extremely arge diploid genome," Theoretical and Applied Genetics, 96: 52-62 (1998).
Van Heusden et al., "AFLP linkage group assignment to the chromosomes of Allium cepa L. via monosomic addition ines," Theoretical and Applied Genetics, 100:480-486 (2000).
Martin et al., "Genetic mapping of expressed sequences in onion and in silico comparisons with rice show scant colinearity," Molecular Genetics and Genomics, 274: 197-204 (2005).
Khrustaleva et al., "The Chromosome Organization of Genes and Some Types of Extragenic DNA in Allium," Acta Hort 369: 43-52 (2012).
Shukla et al., "The Onion Genomic Resource: A genomics and bioinformatics driven resource for onion breeding," Plant Gene, 8: 9-15 (2016).
International Search Report issued in corresponding International Patent Application No. PCT/JP2018/035044 dated Dec. 11, 2018.
Written Opinion issued in corresponding International Patent Application No. PCT/JP2018/035044 dated Dec. 11, 2018.
GenBank: AAA32639.1, https://www.ncbi.nlm.nih.gov/protein/AAA32639.1 (2017).
Van Heusden et al., "AFLP linkage group assignment to the chromosomes of Allium cepa L. via monosomic addition lines," Theoretical and Applied Genetics, 100: 480-486 (2000).
Khrustaleva et al., "The Chromosome Organization of Genes and Some Types of Extragenic DNA in Allium," Acta Hort 969: 43-52 (2012).
Mai et al., "An onion enzyme that makes the eyes water," Nature, 419: 685 (2002).

(Continued)

*Primary Examiner* — Suryaprabha Chunduru
(74) *Attorney, Agent, or Firm* — Morgan, Lewis & Bockius LLP

(57) ABSTRACT

The present invention provides a means for accurately discriminating whether an onion is an onion with no pungent taste and/or tear-inducing property. The present invention relates to a method of discriminating traits of an onion, comprising a first determination step of determining presence of the nucleotide sequence of SEQ ID NO:1 corresponding to alliinase gene 1 in a nucleic acid derived from the onion, and a second determination step of determining presence of the nucleotide sequence of SEQ ID NO:2 corresponding to alliinase gene 2, wherein the onion is discriminated to be an onion with no pungent taste and/or tear-inducing property if the presence of the nucleotide sequence of SEQ ID NO:1 is not determined in the first determination step and the presence of the nucleotide sequence of SEQ ID NO:2 is determined in the second determination step.

5 Claims, 14 Drawing Sheets

Specification includes a Sequence Listing.

(56) References Cited

OTHER PUBLICATIONS

Clark, "Molecular cloning of a cDNA encoding alliinase from onion (*Allium cepa* L.)," A thesis submitted in partial fullfilment of the requirements for the degree of Doctor of Philosophy in Molecular Biology in the University of Canterbury (1993).
Office Action issued in related New Zealand Patent Application No. 762905 dated Aug. 4, 2020.
Office Action issued in corresponding European Patent Application No. 18857824.9 dated Sep. 3, 2020.
Supplementary European Search Report issued in corresponding European Patent Application No. 18857824.9 dated Aug. 12, 2020.
Anonymous, "IBIS-lntegrated Biotechnological Information Services," Aug. 6, 2002, XP55719642.
Anonymous, "IBIS-lntegrated Biotechnological Information Services," Aug. 2, 2002, XP55719638.

\* cited by examiner

SEQ ID NO:1

```
ccgagattac aagtggagca ttaaatatcc atagcagagc taattagcta tggagtctta     60
ccacaaagtt ggcagtaata aaatgccaag ccttcttatt ttgatatgca taatcatgtc    120
Forward primer 1                SF1
ttcatttgtt aacaataata tagctcaagc gaaggtgaca tggagtttga aggcagcaga    180
  SF2
agaggcagaa gcagtggcta atataaactg ttcagggcat gggagagctt ttttggacgg    240
  SR1
aattctttca gatggatctc ctaaatgcga gtgcaatact tgctacactg gtgcagactg    300
ctctgaaaag attacaggtt gctctgctga tgttgccagt ggtgatggac tgtttctaga    360
                                                            SR2
agaatactgg cagcagcaca aggaaaacag tgcagtgctg gtttcaggat ggcacagaat    420
gagctacttt ttcaacccag ttagcaattt catatctttc gagcttgaaa aaacaattaa    480
agaactacat gagatagtcg gaaatgctgc tgcaaaggac aggtacattg tgtttggagt    540
aggggtgact caactcatcc atggattggt catctctctt tcaccaaata tgactgccac    600
tccttgtgca ccacaatcta aagttgttgc tcatgcccct tattatccgg tgtttagaga    660
acaaacaaag tactttgaca agaaagggta cgagtggaaa ggaaatgcag cggattacgt    720
gaacacttca actccagagc aattcattga gatggttact tcacctaata acccagaagg    780
tctgcttcgc catgaagtaa taagggatg caaatccatc tacgatatgg tttactactg    840
            SR3
gcctcattac acccaatca agtacaaagc cgatgaagat atcatgttgt tacaatgtc     900
F3
taaatacact ggacactctg gtagtcgatt tgggtgggca ctgataaagg atgaaactgt    960
gtataataaa ttgttgaatt acatgacaaa gaacacggag ggcacttccc gagaaacaca   1020
gctacgatcg ctcaaaattc taaagaagt tatagcaatg gttaaaacac agaaaggcac   1080
catgcgcgac ctcaacacat ttggttttca gaaactaaga gagaggtggg taaatatcac   1140
ttcattgctc gataaatccg acagattctc ctatcaaaag cttccacaaa gtgaatattg   1200
```

Fig. 7-2

SEQ ID NO:1

```
caattacttc aggagaatga gacctccatc cccatcttat gcatgggtga agtgtgaatg        1260
                                        R3
ggaagaagac aaagattgct accagacatt tcaaaatggg cgtatcaata cgcaaagtgg        1320
                         SF3
agagggtttc gaagcaggta gtcgttatgt gcgtttgagt ttgatcaaga caaaagatga        1380
            SF4
ttttgatcaa ctaatgtact atttgaagaa tatggttgaa gcaaagagga agactcctct        1440
catcaaacaa ctttccaatg atcagatctc ccgccgtcct ttcatttaag tactcatgtt        1500
                                SR4
atgtattgct ctgctgtttt gttagtgtat gactatgttc atacatccta atgctatggt        1560
agtaaggagt atctttctat gcaataaata aagttcatgt ttgtgatcat gtatgggcta        1620
                               Reverse primer 2
ctatgatttt ataataaaat caattttcat ataaaaaaaa aaa                         1663
```

Fig. 8-1

SEQ ID NO:2

| | | | | | |
|---|---|---|---|---|---|
| ccacaaagtt ggcagt|agta aaatgccaag cctacttatt ttgatatgca taatcatgtc | | | | | 60 |

Forward primer 1                 UF1 ttcatttgtc aacaataata tagctcaagg gaaggtgaca tggagtttga aggcagcaga     120
UF2 agaggcggag gcagtggcca atataaactg ttcagggcat ggaagagctt ttttggatgg     180
      UR1 aattctttca gatggctctc ctaaatgcga gtgcaatact tgctacactg gtgcagattg     240
ctctcaaaag attacaggtt gctctgcgga tgttgccagg ttaatatttc tctgttcttc     300
acaatacatg gtagtttaac tttatatcaa acacactgga caatatttaa tgacatgctt     360
aaggaattga atgatatatt gtatacacag tgstgatgga ctgwttcttg aggaatattg     420
                                                       UR2 gcagcascac maggaaaaca gtgcagtgct cgtttcagga tggcacagaa tgagctactt     480
tttcaaccca gytagcaatt tcatatcgtt cgagcttgaa aaaacaatta aggaactaca     540
tgagatagtc ggaaatgctg ctgcaaagga caggtacatt gtgtttggag tcggggtgac     600
tcaactcatc catggattgg tcatctytct ttcaccaaat atgactgcca ctccttgtgc     660
accacaatct aaagttgttg ctcatgcccc tttttatccg gtaactctac gcatgtttct     720
aagttgaact acctagagat aactgtttat ttcttatgta ctcgtgtgac tgacttaatt     780
tgaacaaatt aaatgataca ggtgttcaga gaacaaacaa atatttttga caagaaaggg     840
tacgagtgga aaggaaatgc agcgaattac gtgaacactt caactcctga gcagttcatt     900
gagatggtta cttcacctaa taacccagaa ggtctgcttc gcaaggaagt aatcaaggga     960
                                                                    UR3 tgcaaatcca tttacgatat ggtttactac tggcctcatt acaccccaat caagtacaaa    1020
                                            F3 gccgacgaag atatcatgtt gtttacaatg tctaaataca ctggacactc tggtagtcga    1080
tttgggtatg tccacatatt attacctcac atctttctct acctataatt aacatattta    1140
agttggttag ttagtaactc atactttaat atcttattaa attaggtggg cgttgataaa    1200

Fig. 8-2

SEQ ID NO:2

| | |
|---|---|
| ggatgaaacc gtgtataata agttgtwaaa ttacatgaca aaaaacacgg aaggcactcc | 1260 |
| tcgggaaaca cagctacgat cgctcaaaat tmtaaaagaa gtcatagcaa tggttaaaac | 1320 |
| acagaaaggc accatgcgtg acctcaacac atttggtttt aagaaactaa gagagaggtg | 1380 |
| ggtaaatatc actgcattgc tggataaatc agacagattc tcctatcaaa agcttccaca | 1440 |
| aagtgaatat tgcaattact tccgaagaat gagacctcca tccccatgta tgtataccag | 1500 |
| tatattatca tttattgaaa gatataatat tatagattat aaacataaca atgyagcatt | 1560 |
| aatcaatgat atatatatac acgatgacag <u>cttatgcatg ggtgaagtgt gaatgg</u>gaag<br>                      R3 | 1620 |
| aagacaaaga ttgctaccag <u>acatttcaaa atggacgyat caacacacaa agtggagagg</u><br>                    UF3 | 1680 |
| <u>gtttcgaagc gggcagtcgt tacgtgcgty</u> tgagtttgat caagacaaag gatgattttg<br>       UF4 | 1740 |
| atcaactcat gtactatttg aagactatgg ttgaagcaaa gaggaagact cctctcatca | 1800 |
| aacaactttc caatgatcag <u>acatcccgcc gtcctttcat ttaagtactc</u> atgttatgta<br>           UR4 | 1860 |
| tcgctcgctg ttttgttagt gtatgactat gttcatacat cctaatgcta tggtcgtaag | 1920 |
| gagttcctat ctttgtaata aataaa<span style="border:1px solid">gttc atgtttgtga tcatgtatgg rctac</span><br>                Reverse primer 2 | 1975 |

ONION DISCRIMINATION METHOD

SEQUENCE LISTING SUBMISSION VIA EFS-WEB

A computer readable text file, entitled "SequenceListing.txt," created on or about Mar. 25, 2020 with a file size of about 9 kb contains the sequence listing for this application and is hereby incorporated by reference in its entirety.

TECHNICAL FIELD

The present invention relates to a method of discriminating whether an onion is an onion with no pungent taste and/or tear-inducing property, a primer, a primer set, and a kit used for the method, and a method of breeding an onion using the method.

BACKGROUND ART

Patent Literature 1 discloses that 29 types of alliinases, which are enzymes involved in production of lachrymatory factor (LF), a component causing a pungent taste, are expressed in an onion; that, among them, a specific alliinase consisting of an amino acid sequence as set forth in SEQ ID NO:5 in Patent Literature 1 is the primary alliinase associated with a pungent taste and a tear-inducing property of an onion; and that two lines of tearless and non-pungent onions were produced in which the activity of the specific alliinase was suppressed.

Non Patent Literature 1 also discloses that tearless and non-pungent onions were produced in which the activity of the alliinase was suppressed, as in Patent Literature 1.

Non Patent Literature 2 discloses an amino acid sequence of an alliinase that has a high sequence identity to the amino acid sequence of the specific alliinase disclosed in Patent Literature 1. However, Non Patent Literature 2 does not show the magnitude of contribution of this alliinase to a pungent taste or a tear-inducing property or does not suggest the presence of other alliinases.

Non Patent Literatures 3 to 6 suggest the presence of onion alliinases other than the specific alliinase disclosed in Non Patent Literature 2. However, these literatures disclose neither sequence information of these other alliinases nor explanation of whether they are associated with a pungent taste and a tear-inducing property.

CITATION LIST

Patent Literature

Patent Literature 1: JP Patent No. 5671657 Non Patent Literatures

Non Patent Literature 1: Kato et al. "Production and characterization of tearless and non-pungent onion" DOI: 10.1038/srep23779

Non Patent Literature 2: GenBank Accession No. AAA32639.1

Non Patent Literature 3: King et al. "A low-density genetic map of onion reveals a role for tandem duplication in the evolution of an extremely large diploid genome." Theor Appl Genet 96, 52-62 (1998)

Non Patent Literature 4: Van Heusden, A. W., Shigyo, M., Tashiro, Y., Vrielink-van Ginkel, R. & Kik, C. AFLP linkage group assignment to the chromosomes of *Allium cepa* L. via monosomic addition lines. Theor Appl Genet 100, 480-486 (2000)

Non Patent Literature 5: Martin, W. J. et al. Genetic mapping of expressed sequences in onion and in silico comparisons with rice show scant colinearity. Mol Genet Genom 274, 197-204 (2005)

Non Patent Literature 6: Khrustaleva, L. et al. The chromosome organization of genes and some types of extragenic DNA in Allium. Acta Hort 969, 43-52 (2012)

SUMMARY OF INVENTION

Technical Problem

The onion with suppressed expression of the specific alliinase consisting of the amino acid sequence as set forth in SEQ ID NO:5 in Patent Literature 1, which is disclosed in Patent Literature 1, does not have a pungent taste or a tear-inducing property. However, Patent Literature 1 does not disclose the gene sequence of the specific alliinase or cause of not being expressed (e.g., destruction of regulatory region, transcription factor, or the gene itself). Additionally, Patent Literature 1 does not disclose information on the alliinase gene that was not expressed. Non Patent Literature 1 also discloses that tearless and non-pungent onions were produced in which the activity of the alliinase was suppressed, as in Patent Literature 1, but does not disclose the complete sequence of the alliinase with suppressed expression or cause of the suppressed expression.

The onion alliinase gene is a multicopy gene. As disclosed in Patent Literature 1, there are 29 alliinase genes that are expressed, and even more alliinase genes are present in an onion if genes that are not expressed are included. Additionally, Non Patent Literatures 2 to 6 also indicate the presence of alliinase genes other than the specific alliinase genes disclosed in Patent Literature 1. Thus, other alliinase genes might be detected in error, and it was therefore difficult to discriminate whether the onion is an onion with no pungent taste by determining the presence or absence of the gene encoding the specific alliinase disclosed in Patent Literature 1.

The present invention provides a means for discriminating whether an onion is an onion with no pungent taste and/or tear-inducing property by specifically determining the presence of an alliinase gene associated with a pungent taste and a tear-inducing property in the onion in distinction from other genes.

Solution to Problem

The specification discloses the following inventions as solutions to the above-described problem:

(1) A method of discriminating traits of an onion, comprising:

a first determination step of determining presence of the nucleotide sequence of SEQ ID NO:1 in a nucleic acid derived from the onion; and a second determination step of determining presence of the nucleotide sequence of SEQ ID NO:2 in the nucleic acid derived from the onion, wherein the onion is discriminated to be an onion with no pungent taste and/or tear-inducing property if the presence of the nucleotide sequence of SEQ ID NO:1 is not determined in the first determination step and the presence of the nucleotide sequence of SEQ ID NO:2 is determined in the second determination step, and the onion is discriminated to be an onion with a pungent taste and/or a tear-inducing property if the presence of the nucleotide sequence of SEQ ID NO:1 is determined in the first determination step, and the presence of the nucleotide sequence of SEQ ID NO:2 is determined in the second determination step.

(2) The method according to (1), wherein the first determination step comprises determining presence of a first mutation site comprising one or more nucleotides selected from nucleotides at positions 94, 130, 1312, 1348, 187, 358, 791, and 1467 in the nucleotide sequence of SEQ ID NO:1 in the nucleic acid, and the second determination step comprises determining presence of a second mutation site comprising one or more nucleotides selected from nucleotides at positions 34, 70, 1667, 1703, 127, 409, 943, and 1822 in the nucleotide sequence of SEQ ID NO:2 in the nucleic acid.

(3) The method according to (2), wherein the first determination step comprises:

performing a first nucleic acid amplification reaction on a genomic DNA or a cDNA of the onion as a template using a first primer set comprising: a first primer comprising a polynucleotide comprising a nucleotide sequence which is identical or homologous to a partial nucleotide sequence comprising the first mutation site in the nucleotide sequence of SEQ ID NO:1; and/or a second primer comprising a polynucleotide comprising a nucleotide sequence which is identical or homologous to a complementary nucleotide sequence to the partial nucleotide sequence comprising the first mutation site in the nucleotide sequence of SEQ ID NO:1; and confirming an amplification product of the first nucleic acid amplification reaction, and the second determination step comprises:

performing a second nucleic acid amplification reaction on a genomic DNA of the onion as a template using a second primer set comprising: a third primer comprising a polynucleotide comprising a nucleotide sequence which is identical or homologous to a partial nucleotide sequence comprising the second mutation site in the nucleotide sequence of SEQ ID NO:2; and/or a fourth primer comprising a polynucleotide comprising a nucleotide sequence which is identical or homologous to a complementary nucleotide sequence to the partial nucleotide sequence comprising the second mutation site in the nucleotide sequence of SEQ ID NO:2; and confirming an amplification product of the second nucleic acid amplification reaction.

(4) A method of discriminating traits of an onion, comprising a first determination step of determining presence of the nucleotide sequence of SEQ ID NO:1 in a nucleic acid derived from the onion, the first determination step comprising determining presence of a first mutation site comprising one or more nucleotides selected from nucleotides at positions 94, 130, 1312, 1348, 187, 358, 791, and 1467 in the nucleotide sequence of SEQ ID NO:1 in the nucleic acid, wherein the onion is discriminated to be an onion with no pungent taste and/or tear-inducing property if the presence of the nucleotide sequence of SEQ ID NO:1 is not determined in the first determination step, and the onion is discriminated to be an onion with a pungent taste and/or a tear-inducing property if the presence of the nucleotide sequence of SEQ ID NO:1 is determined in the first determination step.

(5) The method according to (4), wherein the first determination step comprises:

performing a first nucleic acid amplification reaction on a genomic DNA or a cDNA of the onion as template using a first primer set comprising: a first primer comprising a polynucleotide comprising a nucleotide sequence which is identical or homologous to a partial nucleotide sequence comprising a first mutation site in the nucleotide sequence of SEQ ID NO:1; and/or a second primer comprising a polynucleotide comprising a nucleotide sequence which is identical or homologous to a complementary nucleotide sequence to the partial nucleotide sequence comprising the first mutation site in the nucleotide sequence of SEQ ID NO:1; and confirming an amplification product of the first nucleic acid amplification reaction.

(6) A method of discriminating traits of an onion, comprising:

discriminating whether the onion is an onion with no pungent taste and/or tear-inducing property according to any of the methods according to (1) to (5); and discriminating whether the onion is an onion with no pungent taste and/or tear-inducing property based on one or more of the following traits as indicator(s):

a) production of pyruvic acid at disruption of onion cells is reduced compared with conventional varieties;

b) the quantity of PRENCSO remaining after disruption of onion cells is greater compared with conventional varieties; and c) production of lachrymatory factor (LF) at disruption of onion cells is reduced compared with conventional varieties.

(7) A method of breeding an onion with no pungent taste and/or tear-inducing property, comprising:

discriminating whether an onion is an onion with no pungent taste and/or tear-inducing property according to any of the methods according to (1) to (6); and using the onion discriminated to be an onion with no pungent taste and/or tear-inducing property to breed an onion.

(8) A primer comprising a first polynucleotide comprising a first nucleotide sequence at the 3' end, wherein the first nucleotide sequence is identical or homologous to a first partial nucleotide sequence of 10 or more consecutive nucleotides comprised in the nucleotide sequence of SEQ ID NO:1, the first partial nucleotide sequence comprising a first nucleotide selected from positions 94, 130, 1312, 1348, 187, 358, 791, and 1467 in the nucleotide sequence of SEQ ID NO:1 within 2 nucleotides from the 3' end.

(9) A primer comprising a second polynucleotide comprising a second nucleotide sequence at the 3' end, wherein the second nucleotide sequence is identical or homologous to a second partial nucleotide sequence of 10 or more consecutive nucleotides comprised in a complementary nucleotide sequence to the nucleotide sequence of SEQ ID NO:1, the second partial nucleotide sequence comprising a nucleotide complementary to a second nucleotide selected from positions 94, 130, 1312, 1348, 187, 358, 791, and 1467 in the nucleotide sequence of SEQ ID NO:1 within 2 nucleotides from the 3' end.

(10) A primer set comprising:

the primer according to (8); and the primer according to (9), wherein the first nucleotide and the second nucleotide are identical to each other, or the first nucleotide is positioned more closely to the 5' end than the second nucleotide in the nucleotide sequence of SEQ ID NO:1.

(11) A primer comprising a third polynucleotide comprising a third nucleotide sequence at the 3' end, wherein the third nucleotide sequence is identical or homologous to a third partial nucleotide sequence of 10 or more consecutive nucleotides comprised in the nucleotide sequence of SEQ ID NO:2, the third partial nucleotide sequence comprising a third nucleotide selected from positions 34, 70, 1667, 1703, 127, 409, 943, and 1822 in the nucleotide sequence of SEQ ID NO:2 within 2 nucleotides from the 3' end.

(12) A primer comprising a fourth polynucleotide comprising a fourth nucleotide sequence at the 3' end, wherein the fourth nucleotide sequence is identical or homologous to a fourth partial nucleotide sequence of 10 or more consecutive nucleotides comprised in a complementary nucleotide sequence to the nucleotide sequence of SEQ ID NO:2, the fourth partial nucleotide sequence comprising a nucleotide complementary to a fourth nucleotide selected from positions 34, 70, 1667, 1703, 127, 409, 943, and 1822 in the nucleotide sequence of SEQ ID NO:2 within 2 nucleotides from the 3' end.

(13) A primer set, comprising:
the primer according to (11); and
the primer according to (12), wherein
the third nucleotide and the fourth nucleotide are identical to each other, or the third nucleotide is positioned more closely to the 5' end than the fourth nucleotide in the nucleotide sequence of SEQ ID NO:2.

(14) A kit for discriminating traits of an onion, comprising:
one selected from the primer according to (8), the primer according to (9), and the primer set according to (10); and
one selected from the primer according to (11), the primer according to (12), and the primer set according to (13).

(15) A marker gene for discriminating a pungent taste and/or a tear-inducing property of an onion, for which the cDNA nucleotide sequence comprises the nucleotide sequence of SEQ ID NO:1.

The specification encompasses the disclosure of JP Patent Application No. 2017-184019, on which the priority of the present application is based.

Advantageous Effects of Invention

According to the onion discrimination method of the present invention, an onion with no pungent taste and/or tear-inducing property, which cannot be discriminated in appearance, can be discriminated accurately.

According to the breeding method of the present invention, a target onion with no pungent taste and/or tear-inducing property can be selected accurately in a setting of breeding a new variety using an onion with no pungent taste and/or tear-inducing property as one of materials.

The primers, the primer sets, and the kit of the present invention can be used to amplify alliinase gene 1 or alliinase gene 2 specifically.

The marker gene of the present invention can be used to detect a pungent taste and/or a tear-inducing property of an onion.

BRIEF DESCRIPTION OF DRAWINGS

FIG. 1-1 shows the alignment results for the nucleotide sequence of SEQ ID NO:1, the nucleotide sequence of SEQ ID NO:2, and the nucleotide sequence of the alliinase gene of GenBank Accession No. AAA32639.1 and the position of each primer.
FIG. 1-2 Continued from FIG. 1-1
FIG. 1-3 Continued from FIG. 1-1
FIG. 1-4 Continued from FIG. 1-1
FIG. 2 shows the detection results for amplification products of PCR on the genomic DNAs of onion #6 with no pungent taste and a control variety as templates using a primer set of the nucleotide sequences of SEQ ID NOS: 3 and 4.

FIG. 3-1 shows the detection results for alliinase gene 1 and alliinase gene 2 in amplification products of PCR on the genomic DNAs of onion #6 with no pungent taste and a control variety as templates using various primer sets.
FIG. 3-2 Continued from FIG. 3-1
FIG. 7-1 shows the positions of primers in the nucleotide sequence of SEQ ID NO:1.
FIG. 7-2 Continued from FIG. 7-1
FIG. 8-1 shows the positions of primers in the nucleotide sequence of SEQ ID NO:2.
FIG. 8-2 Continued from FIG. 8-1.

DESCRIPTION OF EMBODIMENTS

1. Terms

Figure 2:
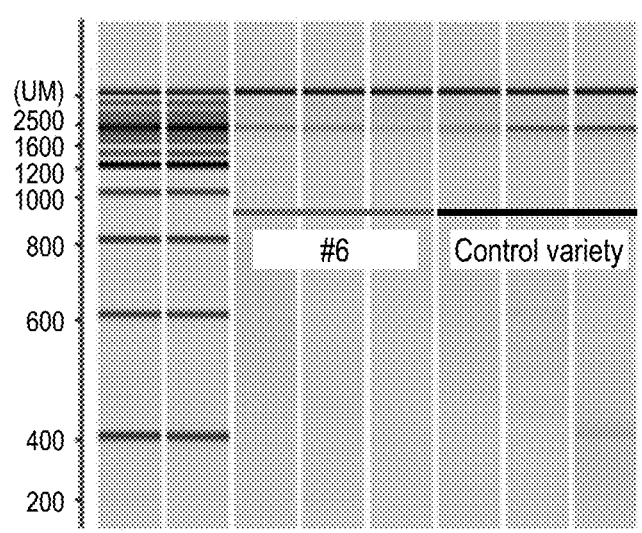

In the specification, "gene 1" refers to a gene encoding an alliinase comprised in the genomic DNA which is transcribed to an mRNA corresponding to a cDNA comprising the nucleotide sequence of SEQ ID NO:1.

Additionally, in the specification, "gene 2" refers to a gene encoding an alliinase, the genomic DNA nucleotide sequence of which comprises the nucleotide sequence of SEQ ID NO:2.

The "gene for which the cDNA nucleotide sequence comprises the nucleotide sequence of SEQ ID NO:1" as used herein refers to a gene for which the nucleotide sequence of the cDNA corresponding to mRNA transcribed from the gene comprises the nucleotide sequence of SEQ ID NO:1.

Messenger RNA (mRNA) as used herein refers to a mature mRNA consisting of exon regions ligated by splicing of a precursor mRNA biosynthesized by RNA polymerase from the genomic DNA as a template in the cell of an onion. The process of production of mRNA (mature mRNA) from genomic DNA is "transcription."

Complementary DNA (cDNA) as used herein refers to a double-stranded DNA consisting of a first DNA complementary to mRNA, which is synthesized by reverse transcriptase using mRNA as a template, and a second DNA complementary to the first DNA (i.e., consisting of a nucleotide sequence obtained by substituting u with t in the nucleotide sequence of mRNA), the single-stranded first DNA, or the single-stranded second DNA. The "nucleotide sequence of the cDNA corresponding to mDNA" as used herein refers to the nucleotide sequence of the second DNA.

In the present invention, "polynucleotide" refers to a deoxyribonucleic acid (DNA) or a ribonucleic acid (RNA), typically a DNA. In RNA, thymine (T) can be substituted with uracil (U). A DNA comprising U, which is synthesized by substituting T with U at one or more positions, can also be used as a DNA. The polynucleotide may comprise modified nucleotides, such as inosine (I), as part thereof.

The polynucleotide may be present as a single-stranded chain or a double-stranded chain. If the polynucleotide is present as a double-stranded chain, it is sufficient that at least one strand is a polynucleotide having characteristics detailed in this specification.

The method of manufacturing a polynucleotide is not particularly limited, and the polynucleotide can be manufactured using a polynucleotide synthesizer.

In the present invention, the "nucleic acid derived from an onion" refers to a genomic DNA, an mRNA, or a cDNA derived from an onion of which traits are to be discriminated (target onion). The genomic DNA, the mRNA, and the cDNA also include amplified fragments of the genomic DNA, amplified fragments of the mRNA, and amplified fragments of the cDNA, respectively.

In the present invention, the expression "a nucleotide sequence Y homologous to a nucleotide sequence X" or "a nucleotide sequence X and a nucleotide sequence Y are homologous to each other" refers to a combination of a DNA chain consisting of the complementary sequence to the nucleotide sequence X and a DNA chain consisting of the nucleotide sequence Y that can form hydrogen bonds enough to hybridize these DNA chains under the annealing condition of a nucleic acid amplification reaction to form a stable double-stranded chain, and the nucleotide sequences X and Y may be partially different. For example, a polynucleotide consisting of the complementary sequence to the nucleotide sequence X and a polynucleotide consisting of the nucleotide sequence Y may comprise some mismatches, such as one mismatch in 10 nucleotides, one mismatch in 20 nucleotides, or one mismatch in 30 nucleotides. Typically, the expression a nucleotide sequence Y "homologous" to a nucleotide sequence X means that the nucleotide sequences X and Y satisfy any of the following relationships:

(A) the nucleotide sequence Y is a nucleotide sequence obtained by deleting, substituting, adding, and/or inserting one or several nucleotides in the nucleotide sequence X;

(B) the nucleotide sequence Y is a nucleotide sequence having a 90% or higher identity to the nucleotide sequence X;

(C) a polynucleotide consisting of the nucleotide sequence Y can be hybridized with a polynucleotide consisting of the nucleotide sequence complementary to SEQ ID NO: X under stringent conditions; and (D) thymine (T) at an arbitrary position in either the nucleotide sequence X or the nucleotide sequence Y is substituted with uracil (U) in the other nucleotide sequence.

In the (A), "one or several" means preferably one or two, and most preferably one.

In the (B), the value of identity indicates a value obtained using a software to calculate the identity between a plurality of nucleotide sequences (e.g., FASTA, DNASIS, and BLAST) under the default setting. The value of nucleotide sequence identity is obtained by counting the number of coincident nucleotides when a pair of nucleotide sequences are aligned at the maximum degree of coincidence and calculating the proportion of the number of coincident nucleotides to the total number of nucleotides in the compared nucleotide sequence. For details of the method of determining identity, refer to, for example, Altschul et al., Nuc Acids. Res. 25, 3389-3402, 1977 and Altschul et al., J. Mol. Biol. 215, 403-410, 1990.

In the (B), the identity is more preferably 95% or higher, more preferably 96% or higher, more preferably 97% or higher, more preferably 98% or higher, and more preferably 99% or higher.

In the (C), the term "stringent conditions" means conditions under which a so-called specific hybrid is formed, and a nonspecific hybrid is not formed. For example, the stringent conditions can be appropriately determined with reference to Green and Sambrook, Molecular Cloning, 4th Ed. (2012), Cold Spring Harbor Laboratory Press. Specifically, stringent conditions can be set for temperature and a salt concentration in a solution for southern hybridization and temperature and a salt concentration in a solution for the washing process in southern hybridization.

<2. First Discrimination Method of the Present Invention>

Firstly, the method of discriminating traits of an onion of the present invention is a method comprising a first determination step of determining presence of the nucleotide sequence of SEQ ID NO:1 in a nucleic acid derived from the onion, and a second determination step of determining presence of the nucleotide sequence of SEQ ID NO:2 in the nucleic acid derived from the onion, wherein the onion is discriminated to be an onion with no pungent taste and/or tear-inducing property if the presence of the nucleotide sequence of SEQ ID NO:1 is not determined in the first determination step and the presence of the nucleotide sequence of SEQ ID NO:2 is determined in the second determination step, and the onion is discriminated to be an onion with a pungent taste and/or a tear-inducing property if the presence of the nucleotide sequence of SEQ ID NO:1 is determined in the first determination step and the presence of the nucleotide sequence of SEQ ID NO:2 is determined in the second determination step. This method is the "first discrimination method" of the present invention.

The present inventors found that, as the nucleotide sequence of the gene encoding alliinase, both the nucleotide sequence of gene 1 and the nucleotide sequence of gene 2 were present in the genomic DNA of a usual onion, whereas the nucleotide sequence of gene 2 was present but the nucleotide sequence of gene 1 was not present in the genomic DNA of an onion with no pungent taste and/or tear-inducing property. The alliinase encoded by the nucleotide sequence of gene 1 is a specific alliinase consisting of the amino acid sequence as set forth in SEQ ID NO:5 disclosed in Patent Literature 1. Although Patent Literature 1 discloses that an onion with suppressed expression of the specific alliinase does not have a pungent taste and/or a tear-inducing property, the cause of not being expressed (e.g., regulatory region, transcription factor, destruction of gene itself) is not disclosed. The present inventors surprisingly found that the nucleotide sequence of gene 1 encoding the specific alliinase was present in the genomic DNA of an onion with no pungent taste and/or tear-inducing property, and that the nucleotide sequence of gene 2 with a high homology to the nucleotide sequence of gene 1, which is not associated with a pungent taste, was present in the genomic DNA. Here, representative examples of the "onion with no pungent taste and/or tear-inducing property" include, but are not limited to, an onion of which seed has been deposited in an International Depository Authority under Accession No. NCIMB 42219, its progenies, and onions with no pungent taste and/or tear-inducing property bred using these onions as one of materials.

The nucleotide sequence of SEQ ID NO:1 is the cDNA nucleotide sequence of alliinase gene 1, and the nucleotide sequence of SEQ ID NO:2 is the genomic DNA nucleotide sequence of alliinase gene 2.

The "determining presence of the nucleotide sequence of SEQ ID NO:1" and "determining presence of the first mutation site (in the nucleotide sequence of SEQ ID NO:1)" in the first determination step mean "determining presence of a nucleotide sequence corresponding to the nucleotide sequence of SEQ ID NO:1" and "determining presence of a nucleotide sequence corresponding to the first mutation site (in the nucleotide sequence of SEQ ID NO:1)," respectively. Similarly, "determining presence of the nucleotide sequence of SEQ ID NO:2" and "determining presence of the second mutation site (in the nucleotide sequence of SEQ ID NO:2)" in the second determination step mean "determining presence of a nucleotide sequence corresponding to the nucleotide sequence of SEQ ID NO:2" and "determining presence of a nucleotide sequence corresponding to the second mutation site (in the nucleotide sequence of SEQ ID NO:2)," respectively.

The "nucleotide sequence corresponding to the nucleotide sequence of SEQ ID NO:1" refers to the genomic DNA nucleotide sequence of an alliinase gene for which the cDNA nucleotide sequence is the nucleotide sequence of SEQ ID NO:1 or the complementary nucleotide sequence thereto if the nucleic acid derived from an onion is a genomic DNA; a nucleotide sequence derived from SEQ ID NO:1 by substitution of T with U if the nucleic acid derived from an onion is an mRNA; or the nucleotide sequence of SEQ ID NO:1 or the complementary nucleotide sequence thereto if the nucleic acid derived from an onion is a cDNA.

The "nucleotide sequence corresponding to the nucleotide sequence of SEQ ID NO:2" refers to the nucleotide sequence of SEQ ID NO:2 or the complementary nucleotide sequence thereto if the nucleic acid derived from an onion is a genomic DNA; a nucleotide sequence derived from the nucleotide sequence of SEQ ID NO:2 by deletion of the intron regions and substitution of T with U if the nucleic acid derived from an onion is an mRNA; or a nucleotide sequence in which intron regions are removed from the nucleotide sequence of SEQ ID NO:2 or the complementary nucleotide sequence thereto if the nucleic acid derived from an onion is a cDNA.

The "nucleotide sequence corresponding to the first mutation site (in the nucleotide sequence of SEQ ID NO:1)" refers to the nucleotide sequence of a site corresponding to the first mutation site in the nucleotide sequence of the genomic DNA of an alliinase gene for which the cDNA nucleotide sequence is the nucleotide sequence of SEQ ID NO:1 or the complementary nucleotide sequence thereto if the nucleic acid derived from an onion is a genomic DNA; the nucleotide sequence of a site corresponding to the first mutation site in a nucleotide sequence derived from SEQ ID NO:1 by substitution of T with U if the nucleic acid derived from an onion is an mRNA; or the first mutation site in the nucleotide sequence of SEQ ID NO:1 or the complementary nucleotide sequence thereto if the nucleic acid derived from an onion is a cDNA.

The "nucleotide sequence corresponding to the second mutation site (in the nucleotide sequence of SEQ ID NO:2)" refers to the second mutation site in the nucleotide sequence of SEQ ID NO:2 or the complementary nucleotide sequence thereto if the nucleic acid derived from an onion is a genomic DNA; the nucleotide sequence of a site corresponding to the second mutation site in a nucleotide sequence derived from the nucleotide sequence of SEQ ID NO:2 by deletion of the intron regions and substitution of T with U if the nucleic acid derived from an onion is an mRNA; or the nucleotide sequence of a site corresponding to the second mutation site in the nucleotide sequence derived from the nucleotide sequence of SEQ ID NO:2 by deletion of the intron regions, or the complementary nucleotide sequence thereto if the nucleic acid derived from an onion is a cDNA.

It is preferable to analyze a genomic DNA as a nucleic acid derived from an onion because the quantity does not change depending on the growth stage of the target onion or the site thereof. Furthermore, a genomic DNA is preferable because whether an analysis is being performed under appropriate conditions can be confirmed by confirming not only the presence or absence of the nucleotide sequence of gene 1, but also the presence of the nucleotide sequence of gene 2, which is present regardless of the presence of a pungent taste of an onion in the first discrimination method of the present invention.

The "first determination step" will be explained in detail below.

The first determination step is a step of determining the presence of the nucleotide sequence of SEQ ID NO:1 in a nucleic acid derived from an onion. In the step, preferably, a nucleotide sequence comprising at least a partial nucleotide sequence of the nucleotide sequence of SEQ ID NO:1 or of a nucleotide sequence derived from SEQ ID NO:1 by substitution of T with U or the complementary nucleotide sequence to the partial nucleotide sequence is detected in the nucleic acid derived from the onion.

When the nucleotide sequence of SEQ ID NO:1, which is the cDNA nucleotide sequence of gene 1, and the nucleotide sequence of SEQ ID NO:2, which is the genomic DNA nucleotide sequence of gene 2, were aligned to obtain the maximum matching, some mismatching nucleotides were found in regions with a high homology as shown in FIGS. 1-1, 1-2, 1-3, and 1-4. Specifically, positions 94, 130, 1312, 1348, 187, 358, 791, and 1467 in the nucleotide sequence of SEQ ID NO:1 and positions 34, 70, 1667, 1703, 127, 409, 943, and 1822 in the nucleotide sequence of SEQ ID NO:2 are mismatching nucleotides comprised in the regions with a high homology.

Accordingly, in the first determination step, it is preferable to determine the presence of a first mutation site comprising one or more nucleotides selected from nucleotides at positions 94, 130, 1312, 1348, 187, 358, 791, and 1467 in the nucleotide sequence of SEQ ID NO:1. This enables to specifically detect the nucleotide sequence of SEQ ID NO:1 comprised in an nucleic acid derived from an onion, without detecting the nucleotide sequence of SEQ ID NO:2 in error.

As a specific means for determining the presence of the first mutation site in the nucleotide sequence of SEQ ID NO:1 in the nucleic acid derived from the onion, it is preferable to perform a first nucleic acid amplification reaction using the following first primer set and a nucleic acid derived from an onion, in particular, a genomic DNA or a cDNA as a template and to confirm an amplification product of the first nucleic acid amplification reaction.

A first primer set preferably comprises at least either one of a first primer comprising a polynucleotide comprising a nucleotide sequence which is identical or homologous to a partial nucleotide sequence comprising the first mutation site in the nucleotide sequence of SEQ ID NO:1, and a second primer comprising a polynucleotide comprising a nucleotide sequence which is identical or homologous to the complementary nucleotide sequence to a partial nucleotide sequence comprising the first mutation site in the nucleotide sequence of SEQ ID NO:1, and particularly preferably both the first and second primers.

Examples of a preferred embodiment of the first primer include a first primer comprising a first polynucleotide comprising a first nucleotide sequence at the 3' end which is identical or homologous to a first partial nucleotide sequence of 10 or more consecutive nucleotides comprised in the nucleotide sequence of SEQ ID NO:1, the first partial nucleotide sequence comprising a first nucleotide selected from positions 94, 130, 1312, 1348, 187, 358, 791, and 1467 in the nucleotide sequence of SEQ ID NO:1 within 2 nucleotides from the 3' end.

Examples of a preferred embodiment of the second primer include a second primer comprising a second polynucleotide comprising a second nucleotide sequence at the 3' end which is identical or homologous to a second partial nucleotide sequence of 10 or more consecutive nucleotides comprised in the complementary nucleotide sequence to the nucleotide sequence of SEQ ID NO:1, the second partial nucleotide sequence comprising a nucleotide complementary to a second nucleotide selected from positions 94, 130, 1312, 1348, 187, 358, 791, and 1467 in the nucleotide sequence of SEQ ID NO:1 within 2 nucleotides from the 3' end.

The preferred embodiment of the first primer will be explained below.

The first partial nucleotide sequence described in association with the first primer is a partial nucleotide sequence of 10 or more consecutive nucleotides, preferably 15 or more consecutive nucleotides, more preferably 17 or more consecutive nucleotides, more preferably 20 or more consecutive nucleotides, and more preferably 23 or more consecutive nucleotides comprised in the nucleotide sequence of SEQ ID NO:1. Of note, to prevent a nonspecific hybrid formation between the primer and a region other than the end region of the target nucleic acid to be amplified, it is well-known that designing a primer with the number of primer nucleotides within the above-described ranges, in particular 17 or more nucleotides, is desirable (for example, refer to takara-bio.co.jp/prt/pdfs/prt3-1.pdf). The upper limit of the number of nucleotides in the first partial nucleotide sequence is not particularly limited, and is preferably 50 or fewer nucleotides, more preferably 40 or fewer nucleotides, more preferably 35 or fewer nucleotides, and more preferably 30 or fewer nucleotides. When the first partial nucleotide sequence comprises the first nucleotide as a nucleotide within 2 nucleotides from the 3' end, preferably as a nucleotide at the 3' end, a region on the 3' end side from a nucleotide corresponding to the first nucleotide in the nucleotide sequence on the sense chain of gene 1 in the template nucleic acid is specifically elongated from the 3' end of the first primer in the first nucleic acid amplification reaction.

The first polynucleotide comprises the first nucleotide sequence which is identical or homologous to the first partial nucleotide sequence at the 3' end. Here, the term "homologous" is defined as described above. More preferably, the first partial nucleotide sequence and the first nucleotide sequence are identical to each other preferably in a region of 3 nucleotides at the 3' end, more preferably in a region of 5 nucleotides at the 3' end, more preferably a region of 8 nucleotides at the 3' end, and more preferably in a region of 10 nucleotides at the 3' end (further preferably in a region of 15 nucleotides at the 3' end if the length of the first partial nucleotide sequence is 15 or more nucleotides, further preferably in a region of 17 nucleotides at the 3' end if the length of the first partial nucleotide sequence is 17 or more nucleotides, and further preferably in a region of 20 nucleotides at the 3' end if the length of the first partial nucleotide sequence is 20 or more nucleotides) and are homologous to each other in the remaining region on the 5' end side. Specific examples of the first nucleotide sequence include the nucleotide sequence as set forth in SEQ ID NO:5, 6, 7, or 8 and a partial nucleotide sequence comprising preferably 15 or more consecutive nucleotides, more preferably 17 or more consecutive nucleotides, and more preferably 20 or more consecutive nucleotides from the 3' end of the nucleotide sequence as set forth in SEQ ID NO:5, 6, 7, or 8. The expression that the first polynucleotide "comprises the first nucleotide sequence at the 3' end" encompasses both a case where the whole nucleotide sequence of the first polynucleotide consists only of the first nucleotide sequence and a case where the first polynucleotide comprises the first nucleotide sequence and a further nucleotide sequence linked to the first nucleotide sequence at the 5' end thereof. It is sufficient that the further nucleotide sequence does not substantially inhibit the first nucleic acid amplification reaction, and the number of nucleotides thereof is, for example, 20 or fewer nucleotides, preferably 10 or fewer nucleotides, more preferably 5 or fewer nucleotides, and more preferably 1 or 2 nucleotides.

Figures 1, 3:
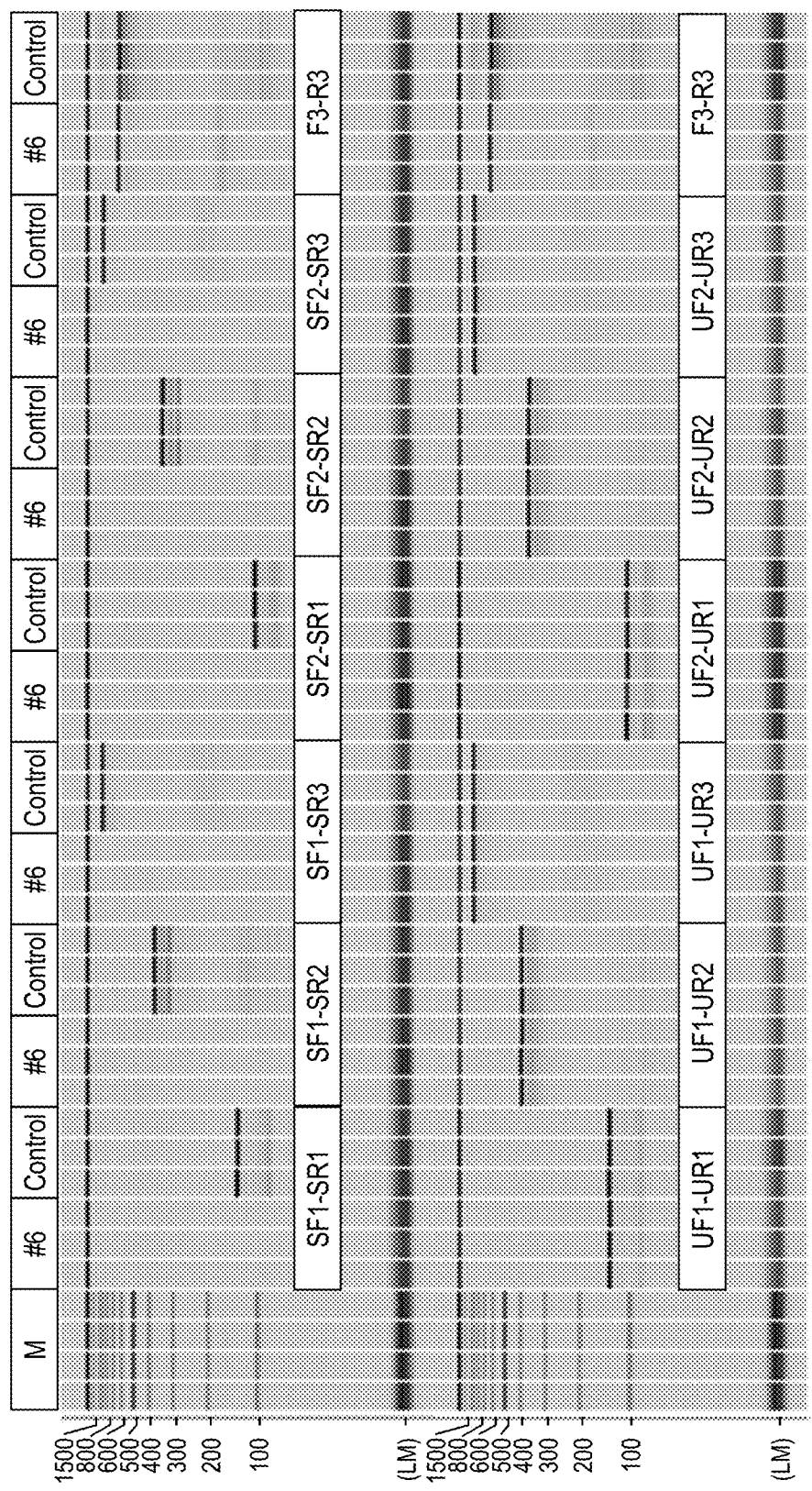
Figures 2, 3:
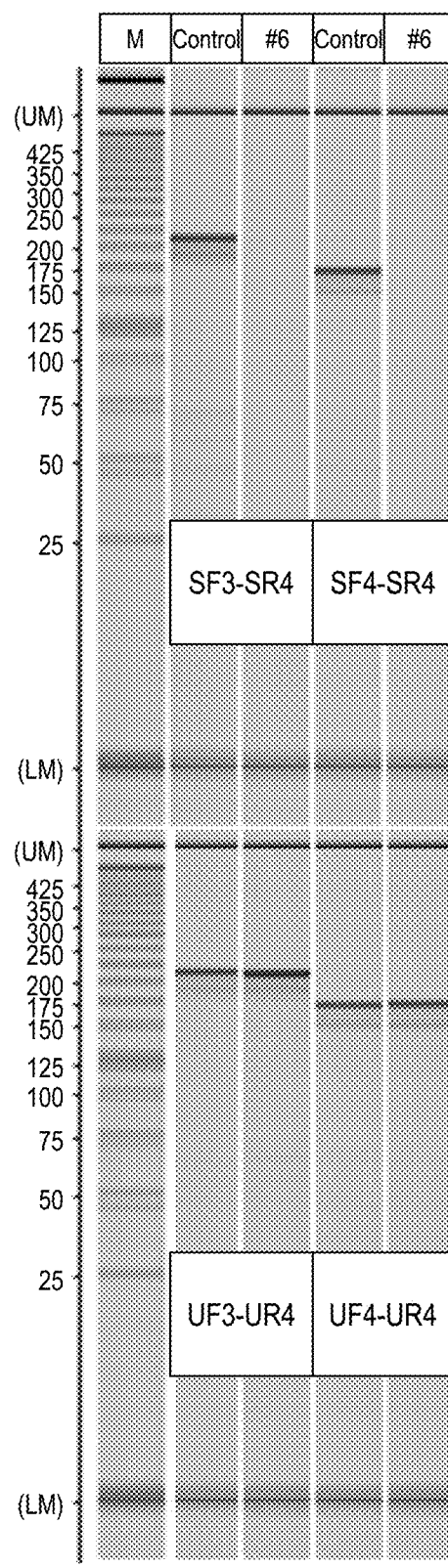

In the specification, the first primers comprising the first polynucleotide consisting of the nucleotide sequences of SEQ ID NOS: 5, 6, 7, and 8 are referred to as SF1, SF2, SF3, and SF4, respectively, and their positions in the nucleotide sequence of SEQ ID NO:1 are shown in FIGS. 7-1 and 7-2.

The first primer may consist of the first polynucleotide or may comprise the first polynucleotide and useful chemical structures such as a labeling tag, a labeling substance, and immobilization tag added to the first polynucleotide. Such useful chemical structures can be detected.

If the first primer set comprises the first primer, the other primer is preferably a primer comprising a polynucleotide comprising a nucleotide sequence at the 3' end which is identical or homologous to a partial nucleotide sequence of 10 to 50 consecutive nucleotides, preferably 15 to 30 consecutive nucleotides comprised in the complementary nucleotide sequence to the nucleotide sequence of SEQ ID NO:1, which is complementary to a region positioned more closely to the 3' end than the first nucleotide in the nucleotide sequence of SEQ ID NO:1, and more preferably the second primer.

The preferred embodiment of the second primer will be explained below.

The second partial nucleotide sequence described in association with the second primer is a partial nucleotide sequence of 10 or more consecutive nucleotides, preferably 15 or more consecutive nucleotides, more preferably 17 or more consecutive nucleotides, more preferably 20 or more consecutive nucleotides, and more preferably 23 or more consecutive nucleotides comprised in the complementary nucleotide sequence to the nucleotide sequence of SEQ ID NO:1. The upper limit of the number of nucleotides in the second partial nucleotide sequence is not particularly limited, and is preferably 50 or fewer nucleotides, more preferably 40 or fewer nucleotides, more preferably 35 or fewer nucleotides, and more preferably 30 or fewer nucleotides. When the second partial nucleotide sequence comprises the complementary nucleotide of the second nucleotide as a nucleotide within 2 nucleotides from the 3' end, preferably as a nucleotide at the 3' end, a region on the 3' end side from a nucleotide corresponding to the complementary nucleotide of the second nucleotide in the nucleotide sequence on the antisense chain of gene 1 in the template nucleic acid is specifically elongated from the 3' end of the second primer in the first nucleic acid amplification reaction.

The second polynucleotide comprises the second nucleotide sequence which is identical or homologous to the second partial nucleotide sequence at the 3' end. Here, the term "homologous" is defined as described above. More preferably, the second partial nucleotide sequence and the second nucleotide sequence are identical to each other, preferably in a region of 3 nucleotides at the 3' end, more preferably in a region of 5 nucleotides at the 3' end, more preferably in a region of 8 nucleotides at the 3' end, and more preferably in a region of 10 nucleotides at the 3' end (further preferably in a region of 15 nucleotides at the 3' end if the length of the second partial nucleotide sequence is 15 or more nucleotides, further preferably in a region of 17 nucleotides at the 3' end if the length of the second partial nucleotide sequence is 17 or more nucleotides, and further preferably in a region of 20 nucleotides at the 3' end if the length of the second partial nucleotide sequence is 20 or more nucleotides) and are homologous to each other in the remaining region on the 5' end side. Specific examples of the second nucleotide sequence include the nucleotide sequence as set forth in SEQ ID NO:9, 10, 11, or 12 and a partial nucleotide sequence comprising preferably 15 or more consecutive nucleotides, more preferably 17 or more consecutive nucleotides, and more preferably 20 or more consecutive nucleotides from the 3' end of the nucleotide sequence as set forth in SEQ ID NO:9, 10, 11, or 12. The expression that the second polynucleotide "comprises the second nucleotide sequence at the 3' end" encompasses both a case where the whole nucleotide sequence of the second polynucleotide consists only of the second nucleotide sequence and a case where the second polynucleotide comprises the second nucleotide sequence and a further nucleotide sequence linked to the second nucleotide sequence at the 5' end thereof. It is sufficient that the further nucleotide sequence does not substantially inhibit the first nucleic acid amplification reaction, and the number of nucleotides thereof is, for example, 20 or fewer nucleotides, preferably 10 or fewer nucleotides, more preferably 5 or fewer nucleotides, and more preferably 1 or 2 nucleotides.

In the specification, the second primers comprising the second polynucleotides consisting of the nucleotide sequences of SEQ ID NOS: 9, 10, 11, and 12 are referred to as SR1, SR2, SR3, and SR4, respectively, and their positions in the nucleotide sequence of SEQ ID NO:1 are shown in FIGS. 7-1 and 7-2.

The second primer may consist of the second polynucleotide or may comprise the second polynucleotide and useful chemical structures such as a labeling tag, a labeling substance, and immobilization tag added to the second polynucleotide. Such useful chemical structures can be detected.

If the first primer set comprises the second primer, the other primer is preferably a primer comprising a polynucleotide comprising a nucleotide sequence at the 3' end which is identical or homologous to a partial nucleotide sequence of 10 to 50 consecutive nucleotides, preferably 15 to 30 consecutive nucleotides comprised in the nucleotide sequence of SEQ ID NO:1, which is a region positioned more closely to the 5' end than the second nucleotide in the nucleotide sequence of SEQ ID NO:1, and more preferably the first primer.

If the first primer set is a combination of the first primer and the second primer, it is sufficient that the first primer and the second primer are selected so that the first nucleotide and the second nucleotide are identical to each other, or the first nucleotide is positioned more closely to the 5' end than the second nucleotide in the nucleotide sequence of SEQ ID NO:1. In a preferred embodiment in which the first primer set is a combination of the first primer and the second primer, the first nucleotide for the first primer is at position 94, 130, 1312, or 1348 in the nucleotide sequence of SEQ ID NO:1, and the second nucleotide for the second primer is at position 187, 358, 791, or 1467 in SEQ ID NO:1, provided that the first nucleotide is identical to the second nucleotide or is positioned more closely to the 5' end than the second nucleotide in the nucleotide sequence of SEQ ID NO:1.

The "second determination step" will be explained in detail below.

The second determination step is a step of determining the presence of the nucleotide sequence of SEQ ID NO:2 in a nucleic acid derived from an onion. In the step, preferably, a nucleotide sequence comprising at least a partial nucleotide sequence of the nucleotide sequence of SEQ ID NO:2 or of a nucleotide sequence derived from SEQ ID NO:2 substitution of T with U or the complementary nucleotide sequence to the partial nucleotide sequence is detected in the nucleic acid derived from the onion.

In the second determination step, it is preferable to determine the presence of a second mutation site comprising one or more nucleotides selected from nucleotides at positions 34, 70, 1667, 1703, 127, 409, 943, and 1822 in the nucleotide sequence of SEQ ID NO:2. This enables to specifically detect the nucleotide sequence of SEQ ID NO:2 comprised in a nucleic acid derived from an onion, without detecting the nucleotide sequence of SEQ ID NO:1 in error.

As a specific means for determining the presence of the second mutation site in the nucleotide sequence of SEQ ID NO:2 in the nucleic acid derived from the onion, it is preferable to perform a second nucleic acid amplification reaction using the following second primer set and a nucleic acid derived from an onion, in particular, a genomic DNA as a template and to confirm an amplification product of the second nucleic acid amplification reaction.

A second primer set preferably comprises at least either one of a third primer comprising a polynucleotide comprising a nucleotide sequence which is identical or homologous to a partial nucleotide sequence comprising the second mutation site in the nucleotide sequence of SEQ ID NO:2, and a fourth primer comprising a polynucleotide comprising a nucleotide sequence which is identical or homologous to the complementary nucleotide sequence to the partial nucleotide sequence comprising the second mutation site in the nucleotide sequence of SEQ ID NO:2, and particularly preferably both the third and fourth primers.

Examples of a preferred embodiment of the third primer include a third primer comprising a third polynucleotide comprising a third nucleotide sequence at the 3' end which is identical or homologous to a third partial nucleotide sequence of 10 or more consecutive nucleotides comprised in the nucleotide sequence of SEQ ID NO:2 comprising a third nucleotide selected from positions 34, 70, 1667, 1703, 127, 409, 943, and 1822 in the nucleotide sequence of SEQ ID NO:2 within 2 nucleotides from the 3' end.

Examples of a preferred embodiment of the fourth primer include a fourth primer comprising a fourth polynucleotide comprising a fourth nucleotide sequence at the 3' end which is identical or homologous to a fourth partial nucleotide sequence of 10 or more consecutive nucleotides comprised in the complementary nucleotide sequence to the nucleotide sequence of SEQ ID NO:2 comprising a nucleotide complementary to a fourth nucleotide selected from positions 34, 70, 1667, 1703, 127, 409, 943, and 1822 in the nucleotide sequence of SEQ ID NO:2 within 2 nucleotides from the 3' end.

The preferred embodiment of the third primer will be explained below.

The third partial nucleotide sequence described in association with the third primer is a partial nucleotide sequence of 10 or more consecutive nucleotides, preferably 15 or more consecutive nucleotides, more preferably 17 or more consecutive nucleotides, more preferably 20 or more consecutive nucleotides, and more preferably 23 or more consecutive nucleotides comprised in the nucleotide sequence of SEQ ID NO:2. The upper limit of the number of nucleotides in the third partial nucleotide sequence is not particularly limited, and is preferably 50 or fewer nucleotides, more preferably 40 or fewer nucleotides, more preferably 35 or fewer nucleotides, and more preferably 30 or fewer nucleotides. When the third partial nucleotide sequence comprises the third nucleotide as a nucleotide within 2 nucleotides from the 3' end, preferably as a nucleotide at the 3' end, a region on the 3' end side from a nucleotide corresponding to the third nucleotide in the nucleotide sequence on the sense chain of gene 2 in the template nucleic acid is specifically elongated from the 3' end of the third primer in the second nucleic acid amplification reaction.

The third polynucleotide comprises the third nucleotide sequence which is identical or homologous to the third partial nucleotide sequence at the 3' end. Here, the term "homologous" is defined as described above. More preferably, the third partial nucleotide sequence and the third nucleotide sequence are identical to each other, preferably in a region of 3 nucleotides at the 3' end, more preferably in a region of 5 nucleotides at the 3' end, more preferably in a region of 8 nucleotides at the 3' end, and more preferably in a region of 10 nucleotides at the 3' end (further preferably in a region of 15 nucleotides at the 3' end if the length of the third partial nucleotide sequence is 15 or more nucleotides, further preferably in a region of 17 nucleotides at the 3' end if the length of the third partial nucleotide sequence is 17 or more nucleotides, and further preferably in a region of 20 nucleotides at the 3' end if the length of the third partial nucleotide sequence is 20 or more nucleotides) and are homologous to each other in the remaining region on the 5' end side. Specific examples of the third nucleotide sequence include the nucleotide sequence as set forth in SEQ ID NO:13, 14, 15, or 16 and a partial nucleotide sequence comprising preferably 15 or more consecutive nucleotides, more preferably 17 or more consecutive nucleotides, and more preferably 20 or more consecutive nucleotides from the 3' end of the nucleotide sequence as set forth in SEQ ID NO:13, 14, 15, or 16. The expression that the third polynucleotide "comprises the third nucleotide sequence at the 3' end" encompasses both a case where the whole nucleotide sequence of the third polynucleotide consists only of the third nucleotide sequence and a case where the third polynucleotide comprises the third nucleotide sequence and a further nucleotide sequence linked to the third nucleotide sequence at the 5' end thereof. It is sufficient that the further nucleotide sequence does not substantially inhibit the second nucleic acid amplification reaction, and the number of nucleotides thereof is, for example, 20 or fewer nucleotides, preferably 10 or fewer nucleotides, more preferably 5 or fewer nucleotides, and more preferably 1 or 2 nucleotides.

In the specification, the third primers comprising the third polynucleotide consisting of the nucleotide sequences of SEQ ID NOS: 13, 14, 15, and 16 are referred to as UF1, UF2, UF3, and UF4, respectively, and their positions in the nucleotide sequence of SEQ ID NO:2 are shown in FIGS. 8-1 and 8-2.

The third primer may consist of the third polynucleotide or may comprise the third polynucleotide and useful chemical structures such as a labeling tag, a labeling substance, and immobilization tag added to the third polynucleotide. Such useful chemical structures can be detected.

If the second primer set comprises the third primer, the other primer is preferably a primer comprising a polynucleotide comprising a nucleotide sequence at the 3' end which is identical or homologous to a partial nucleotide sequence of 10 to 50 consecutive nucleotides, preferably 15 to 30 consecutive nucleotides comprised in the complementary nucleotide sequence to the nucleotide sequence of SEQ ID NO:2 which is complementary to a region positioned more closely to the 3' end than the third nucleotide in the nucleotide sequence of SEQ ID NO:2, and more preferably the fourth primer.

The preferred embodiment of the fourth primer will be explained below.

The fourth partial nucleotide sequence described in association with the fourth primer is a partial nucleotide sequence of 10 or more consecutive nucleotides, preferably 15 or more consecutive nucleotides, more preferably 17 or more consecutive nucleotides, more preferably 20 or more consecutive nucleotides, and more preferably 23 or more consecutive nucleotides comprised in the complementary nucleotide sequence to the nucleotide sequence of SEQ ID NO:2. The upper limit of the number of nucleotides in the fourth partial nucleotide sequence is not particularly limited, and is preferably 50 or fewer nucleotides, more preferably 40 or fewer nucleotides, more preferably 35 or fewer nucleotides, and more preferably 30 or fewer nucleotides. When the fourth partial nucleotide sequence comprises the complementary nucleotide of the fourth nucleotide as a nucleotide within 2 nucleotides from the 3' end, preferably as a nucleotide at the 3' end, and a region on the 3' end side from a nucleotide corresponding to the complementary nucleotide of the fourth nucleotide in the nucleotide sequence on the antisense chain of gene 2 in the template nucleic acid is specifically elongated from the 3' end of the fourth primer in the second nucleic acid amplification reaction.

The fourth polynucleotide comprises the fourth nucleotide sequence which is identical or homologous to the fourth partial nucleotide sequence at the 3' end. Here, the term "homologous" is defined as described above. More preferably, the fourth partial nucleotide sequence and the fourth nucleotide sequence are identical to each other, preferably in a region of 3 nucleotides at the 3' end, more preferably in a region of 5 nucleotides at the 3' end, more preferably in a region of 8 nucleotides at the 3' end, and more preferably in a region of 10 nucleotides at the 3' end (further preferably in a region of 15 nucleotides at the 3' end if the length of the fourth partial nucleotide sequence is 15 or more nucleotides, further preferably in a region of 17 nucleotides at the 3' end if the length of the fourth partial nucleotide sequence is 17 or more nucleotides, and further preferably in a region of 20 nucleotides at the 3' end if the length of the fourth partial nucleotide sequence is 20 or more nucleotides) and are homologous to each other in the remaining region on the 5' end side. Specific examples of the fourth nucleotide sequence include the nucleotide sequence as set forth in SEQ ID NO:17, 18, 19, or 20 and a partial nucleotide sequence comprising preferably 15 or more consecutive nucleotides, more preferably 17 or more consecutive nucleotides, and more preferably 20 or more consecutive nucleotides from the 3' end of the nucleotide sequence as set forth in SEQ ID NO:17, 18, 19, or 20. The expression that the fourth polynucleotide "comprises the fourth nucleotide sequence at the 3' end" encompasses both a case where the whole nucleotide sequence of the fourth polynucleotide consists only of the fourth nucleotide sequence and a case where the fourth polynucleotide comprises the fourth nucleotide sequence and a further nucleotide sequence linked to the fourth nucleotide sequence at the 5' end thereof. It is sufficient that the further nucleotide sequence does not substantially inhibit the second nucleic acid amplification reaction, and the number of nucleotides thereof is, for example, 20 or fewer nucleotides, preferably 10 or fewer nucleotides, more preferably 5 or fewer nucleotides, and more preferably 1 or 2 nucleotides.

In the specification, the fourth primers comprising the fourth polynucleotide consisting of the nucleotide sequence of SEQ ID NOS: 17, 18, 19, and 20 are referred to as UR1, UR2, UR3, and UR4, respectively, and their positions in the nucleotide sequence of SEQ ID NO:2 are shown in FIGS. 8-1 and 8-2.

The fourth primer may consist of the fourth polynucleotide or may comprise the fourth polynucleotide and useful chemical structures such as a labeling tag, a labeling substance, and immobilization tag added to the fourth polynucleotide. Such useful chemical structures can be detected.

If the second primer set comprises the fourth primer, the other primer is preferably a primer comprising a polynucleotide comprising a nucleotide sequence at the 3' end which is identical or homologous to a partial nucleotide sequence of 10 to 50 consecutive nucleotides, preferably 15 to 30 consecutive nucleotides comprised in the nucleotide sequence of SEQ ID NO:2, which is a region positioned more closely to the 5' end than the fourth nucleotide in the nucleotide sequence of SEQ ID NO:2, and more preferably the third primer.

If the second primer set is a combination of the third primer and the fourth primer, it is sufficient that the third primer and the fourth primer are selected so that the third nucleotide and the fourth nucleotide are identical to each other, or the third nucleotide is positioned more closely to the 5' end than the fourth nucleotide in the nucleotide sequence of SEQ ID NO:2. In a preferred embodiment in which the second primer set is a combination of the third primer and the fourth primer, the third nucleotide for the third primer is at position 34, 70, 1667, or 1703 in the nucleotide sequence of SEQ ID NO:2, and the fourth nucleotide for the fourth primer is at position 127, 409, 943, or 1822 in SEQ ID NO:2, provided that the third nucleotide is identical to the fourth nucleotide or is positioned more closely to the 5' end than the fourth nucleotide in the nucleotide sequence of SEQ ID NO:2.

In the present invention, both the first nucleic acid amplification reaction and the second nucleic acid amplification reaction (hereinafter referred collectively to as "nucleic acid amplification reaction") can be performed according to a usual polymerase chain reaction (PCR) method.

A nucleic acid, such as a genomic DNA or a cDNA, used as a template can be prepared from an onion according to a usual method.

It is sufficient that a DNA polymerase used for PCR is a thermostable DNA polymerase, and DNA polymerases are not particularly limited. In the present invention, commercially available DNA polymerases can be used. Additionally, primer concentration, number of cycles, temperature, time, compositions of buffer solutions, and other conditions can be appropriately selected depending on the DNA polymerase used, the concentration of each primer, and other conditions.

In the nucleic acid amplification reaction, a polynucleotide fragment comprising a predetermined target region is produced as an amplification product when the nucleic acid derived from the target onion contains a nucleotide sequence to be detected.

The method of confirming the amplification product of the nucleic acid amplification reaction is not particularly limited, and examples thereof include a method in which, after completion of the nucleic acid amplification reaction, the reaction mixture of the nucleic acid amplification reaction is fractioned by gel electrophoresis, and the presence of a band of the size corresponding to the polynucleotide fragment comprising the predetermined target region is confirmed and a method in which the amplification product is labelled and detected. Additionally, the amplification product can also be detected by a real-time PCR method while performing the nucleic acid amplification reaction.

3. Second Discrimination Method of the Present Invention

Secondly, the method of discriminating traits of an onion of the present invention is a method comprising
a first determination step of determining presence of the nucleotide sequence of SEQ ID NO:1 in a nucleic acid derived from the onion,
the first determination step comprising determining presence of a first mutation site comprising one or more nucleotides selected from nucleotides at positions 94, 130, 1312, 1348, 187, 358, 791, and 1467 in the nucleotide sequence of SEQ ID NO:1 in the nucleic acid, wherein
the onion is discriminated to be an onion with no pungent taste and/or tear-inducing property if the presence of the nucleotide sequence of SEQ ID NO:1 is not determined in the first determination step; and
the onion is discriminated to be an onion with a pungent taste and/or a tear-inducing property if the presence of the nucleotide sequence of SEQ ID NO:1 is determined in the first determination step. This method is the "second discrimination method" of the present invention.

The first determination step in the second discrimination method is the same as the first determination step in the first discrimination method. Specific embodiments of the first determination step in the second discrimination method are the same as the specific embodiments of the first determination step in the first discrimination method.

The first determination step in the second discrimination method preferably comprises performing a first nucleic acid amplification reaction using a first primer set comprising at least either one of a first primer and a second primer and a nucleic acid of an onion as a template and confirming an amplification product of the first nucleic acid amplification reaction. The first primer, the second primer, the first primer set, the first nucleic acid amplification reaction, and the method of detecting the amplification product in this embodiment of the second discrimination method are as explained for the first discrimination method.

4. Combination with Further Discrimination Methods

The first or second discrimination method of the present invention may be used in combination with further methods for discriminating an onion with no pungent taste and/or tear-inducing property. By using a plurality of different discrimination methods in combination, an onion with no pungent taste and/or tear-inducing property can be discriminated accurately.

Examples of further methods for discriminating an onion with no pungent taste and/or tear-inducing property include discriminating whether the onion is an onion with no pungent taste and/or tear-inducing property based on one or more of the following traits as indicator(s):

a) production of pyruvic acid at disruption of onion cells is reduced compared with conventional varieties;

b) the quantity of PRENCSO remaining after disruption of onion cells is greater compared with conventional varieties; and c) production of lachrymatory factor (LF) at disruption of onion cells is reduced compared with conventional varieties.

An onion having one or more of the above traits can be discriminated to be an onion with no pungent taste and/or tear-inducing property.

5. Breeding Method

The present invention also provides a method of breeding an onion with no pungent taste and/or tear-inducing property, comprising discriminating whether an onion is an onion with no pungent taste and/or tear-inducing property by the first or second discrimination method of the present invention, and using the onion discriminated to be an onion with no pungent taste and/or tear-inducing property to breed onions.

In a setting of breeding a new variety using an onion with no pungent taste and/or tear-inducing property as one of materials, an onion with no pungent taste and/or tear-inducing property can be accurately selected among onions produced by crossing using the first or second discrimination method of the present invention. The selected onion with no pungent taste and/or tear-inducing property can be used for further breeding.

6. Primers, Primer Sets, Kit

Both the first primer and the second primer are useful as a primer to specifically amplify a part comprising a nucleotide sequence corresponding to the nucleotide sequence of SEQ ID NO:1 in a nucleic acid derived from an onion.

The first primer set comprising the first primer and the second primer in which the first nucleotide and the second nucleotide are identical to each other, or the first nucleotide is positioned more closely to the 5' end than the second nucleotide in the nucleotide sequence of SEQ ID NO:1 is useful as a primer set to specifically amplify a part comprising a nucleotide sequence corresponding to the nucleotide sequence of SEQ ID NO:1 in the nucleic acid derived from the onion.

Both the third primer and the fourth primer are useful as a primer to specifically amplify a part comprising a nucleotide sequence corresponding to the nucleotide sequence of SEQ ID NO:2 in a nucleic acid derived from an onion.

The second primer set comprising the third primer and the fourth primer in which the third nucleotide and the fourth nucleotide are identical to each other, or the third nucleotide is positioned more closely to the 5' end than the fourth nucleotide in the nucleotide sequence of SEQ ID NO:2 is useful as a primer set to specifically amplify a part comprising a nucleotide sequence corresponding to the nucleotide sequence of SEQ ID NO:2 in a nucleic acid derived from an onion.

A kit comprising one or more of these primers or primer sets is useful as a kit to discriminate traits of an onion. The kit can further comprise various components (e.g., DNA polymerase, various buffer solutions, dNTPs) used to perform a nucleic acid amplification reaction and confirm an amplification product.

7. Marker Gene

Alliinase gene 1, for which the cDNA nucleotide sequence comprises the nucleotide sequence of SEQ ID NO:1, is not present in an onion with no pungent taste and/or tear-inducing property and is present in a usual onion with a pungent taste and/or a tear-inducing property. Therefore, alliinase gene 1 is useful as a marker gene to detect a pungent taste and/or a tear-inducing property of an onion. If alliinase gene 1 is detected in a nucleic acid derived from an onion, the onion can be discriminated to be an onion with a pungent taste and/or a tear-inducing property. If alliinase gene 1 is not detected in a nucleic acid derived from an onion, the onion is discriminated to be an onion with no pungent taste and/or tear-inducing property.

8. Further Inventions

The present invention further includes the following inventions A to C:

A. A plant body of an onion with no pungent taste and/or tear-inducing property discriminated to be an onion with no pungent taste and/or tear-inducing property by the first or second discrimination method of the present invention, a progeny thereof, or a part thereof.

B. A method of manufacturing a plant body of an onion with no pungent taste and/or tear-inducing property, a progeny thereof, or a part thereof, comprising the following steps:

(i) a step of inducing a mutation in an onion seed;

(ii) a step of cultivating the onion seed with the induced mutation to obtain a plant body of the onion or a part thereof, and (iii) a step of discriminating and selecting the plant body of an onion with no pungent taste and/or tear-inducing property or a part thereof by the first or second discrimination method of the present invention from plant bodies or parts thereof of the obtained onions.

C. A method of manufacturing a plant body of an onion with no pungent taste and/or tear-inducing property, a progeny thereof, or a part thereof, comprising crossing a first onion discriminated to be an onion with no pungent taste and/or tear-inducing property by the first or second discrimination method of the present invention and a second onion.

The description in Patent Literature 1 may be referred to for specific aspects of the inventions A to C.

EXAMPLES

Example 1: Acquiring the Gene Sequence of Alliinase Associated with a Pungent Taste and/or a Tear-Inducing Property of an Onion Three bulbs of a tearless and non-pungent onion #6 disclosed in Patent Literature 1 (the seed of onion #6 has been deposited in an International Depository Authority under Accession No. NCIMB 42219. Hereinafter, the onion is referred to as "onion #6") and three bulbs of an onion having a pungent taste obtained by repeating the same number of times of self-reproduction of the same variety as onion #6 (hereinafter referred to as "control variety") as control bulbs were rapidly frozen with liquid nitrogen and then cryopreserved at −80° C. The skin of each frozen onion bulb was peeled, 100 mg of onion tissue was measured and taken out, and a total RNA was collected using the RNeasy Plant Mini kit (manufactured by Qiagen) according to the attached manual. Further, the collected total RNA was subjected to DNase treatment using the RNeasy Mini Kit (manufactured by Qiagen) and the RNase-Free DNase Set (manufactured by Qiagen). The treated total RNA was subjected to concentration measurement and quality confirmation using the Nanodrop (manufactured by Nanodrop Technologies) and the Agilent 2100 Bioanalyzer (manufactured by Agilent Technologies). In the quality confirmation, it was confirmed that samples had A260/A280 absorbance ratios of 1.8 or higher and RNA Integrity Numbers of 8.0 or higher, and a sequence library was prepared using the TruSeq RNA Sample Prep Kit (manufactured by Illumina) according to the attached manual. The prepared sequence library was subjected to sequence analysis using a next-generation sequencer HiSeq (manufactured by Illumina) under the following conditions:
(Sequence Conditions)

Analytical method, paired end sequencing; number of specimens, 6; number of lanes, 3; read nucleotide length, 100 nucleotides/read
(Data Processing)

The obtained data were subjected to the following information processing:

Data with a low fluorescence purity were removed using a formula called Chastity. "Chastity" is represented by a formula of "I1/(I1+I2)," where the largest value of signals from 4 different nucleotides is I1 and the second largest value is I2. In this example, data were selected under a condition of "I1/(I1+I2)>0.6."

The selected data were sorted out by specimen according to the specimen unique index information.

Reads comprising an adaptor sequence were removed, and read pairs in which the Quality Value was 20 or higher for 90% or more of the comprised nucleotides were further extracted. De novo assembly was performed for data of all these specimens using Trinity (trinityrnaseq.sourceforge.net/index.html version 2013-02-25).

The assembly data (estimated transcript sequence) were annotated by BLAST search. The BLASTX was used as the annotation program, and the amino acid sequences in RefSeq-Fungi, RefSeq-Microbial, RefSeq-Plant of NCBI and the amino acid sequences and the gene sequences (converted to amino acid sequence) registered under Allieae in the NCBI classification were integrated and used as the database. The BLASTX parameter used was evalue 1E-5/num_alignments 100/outfmt "6 qseqid sseqid pident length mismatch gapopen qstart qend sstart send evalue bitscore qlen slen stitle qcovs qcovhsp"/, and default conditions were used for others.

As a result, a cDNA nucleotide sequence encoding alliinase comprising "amino acid sequence 5" disclosed in Patent Literature 1 was acquired. The cDNA nucleotide sequence of "amino acid sequence 5" encoding alliinase is shown as SEQ ID NO:1 in the sequence listing.

Example 2: Acquisition of Sequences of Other Alliinases with a High Homology to the Alliinase Encoded by the Nucleotide Sequence of SEQ ID NO:1

A forward primer corresponding to the end part of the nucleotide sequence of SEQ ID NO:1 encoding alliinase that comprises the start codon and a reverse primer corresponding to the end part of the nucleotide sequence that comprises the stop codon were prepared, 100 mg each of samples were collected from both onion #6 and the control variety used in Example 1, the genomic DNA was prepared using the DNeasy Plant Mini Kit (manufactured by Qiagen) according to the attached manual, and a polymerase chain reaction (PCR) was performed using the prepared genomic DNA as a template. Amplification products were analyzed using the MultiNA Electrophoresis System (manufactured by Shimadzu Corporation). The nucleotide sequences of the primers are as shown below, and the positions of the primers are shown in FIGS. 1-1, 1-2, 1-3, and 1-4.

```
Forward primer 1:
                                      (SEQ ID NO: 3)
5'-ATGGAGTCTTACCACAAAGTTGGCAGT-3'

Reverse primer 2:
                                      (SEQ ID NO: 4)
5'-GTAGCCCATACATGATCACAAACATGAAC-3'
```

The results of the analysis of the amplification products by electrophoresis are shown in FIG. 2. Amplification products of the same size were confirmed for both onion #6 and the control variety (FIG. 2). The result of directly sequencing the amplification products confirmed that the product of amplification of the genomic DNA of onion #6 as a template had the genomic DNA nucleotide sequence as set forth in SEQ ID NO:2 exhibiting an approximately 95% identity to the nucleotide sequence of SEQ ID NO:1 in the exon parts (Table 1). Of note, in the nucleotide sequence of SEQ ID NO:1, the first exon is at positions 50 to 339, the second exon is at positions 340 to 651, the third exon is at positions 652 to 935, the fourth exon is at positions 936 to 1235, and the fifth exon is at positions 1236 to 1621. In the nucleotide sequence of SEQ ID NO:2, the part corresponding to the first exon in SEQ ID NO:1 is positions 1 to 279, the part corresponding to the second exon in SEQ ID NO:1 is positions 391 to 702, the part corresponding to the third exon in SEQ ID NO:1 is positions 804 to 1087, the part corresponding to the fourth exon in SEQ ID NO:1 is positions 1188 to 1487, and the part corresponding to the fifth exon in SEQ ID NO:1 is positions 1591 to 1975. However, the product of amplification of the genomic DNA of the control variety onion as a template comprised a mixture of the amplification product comprising of genomic DNA fragments of the gene for which the cDNA nucleotide sequence is the nucleotide sequence of SEQ ID NO:1 and the amplification product comprising genomic DNA fragments comprising the nucleotide sequence of SEQ ID NO:2, and clear results could not be obtained by direct sequencing. This result indicated that the control variety onion had, as the alliinase gene, both the alliinase gene for which the cDNA nucleotide sequence comprised the nucleotide sequence of SEQ ID NO:1 (hereinafter referred to as "alliinase gene 1") and the alliinase gene for which the genomic DNA nucleotide sequence comprised the nucleotide sequence of SEQ ID NO:2 (hereinafter referred to as "alliinase gene 2") and that onion #6 had alliinase gene 2 but did not have alliinase gene 1 as alliinase genes. Of note, alliinase gene 2 appears to be a pseudogene, which is not expressed, because RNA corresponding to this gene was not detected in the RNA-seq analysis of Example 1.

TABLE 1

| | 1st exon | 2nd exon | 3rd exon | 4th exon | 5th exon + 3'UTR |
|---|---|---|---|---|---|
| Identity between the nucleotide sequence of SEQ ID NO: 1 and the nucleotide sequence of SEQ ID NO: 2 | 266/279 = 95.3% | 298/312 = 95.5% | 273/284 = 96.1% | 280/300 = 93.3% | 363/385 = 94.3% |

Example 3: Preparation of Primers that can Distinguish a Tearless and Non-Pungent Onion and a Usual Onion To prepare primers to detect alliinase gene 1 and alliinase gene 2 specifically, the nucleotide sequences of the alliinase genes of SEQ ID NO:1, SEQ ID NO:2, and GenBank Accession No. AAA32639.1 were compared, and primers that specifically amplified only either one of alliinase gene 1 and alliinase gene 2 were prepared, wherein one or more nucleotides at the 3' end of each primer are identical to only either one of the nucleotide sequence of SEQ ID NO:1 and the nucleotide sequence of SEQ ID NO:2 at the corresponding positions. As control primers, primers were prepared for a part common to the nucleotide sequence of SEQ ID NO:1 and the nucleotide sequence of SEQ ID NO:2. The nucleotide sequence of each primer is shown in Table 2, and the positions of the primers are shown in FIGS. 7-1, 7-2, 8-1, and 8-2.

A mixture of UF3 primers (SEQ ID NO:15) that comprised T or C at the position of Y were used.

PCR was performed on the genomic DNAs of onion #6 and the control variety prepared in Example 2 as templates using the prepared primers, and amplification products were analyzed using the MultiNA Electrophoresis System (manufactured by Shimadzu Corporation). The results are shown in FIGS. 3-1 and 3-2. Combinations of the forward primer and the reverse primer used are shown in FIGS. 3-1 and 3-2.

When the genomic DNA of onion #6 was used as a template, amplification products corresponding to the nucleotide sequence of SEQ ID NO:2 were obtained, and when the genomic DNA of the control variety was used as a template, both amplification products corresponding to the nucleotide sequence of SEQ ID NO:1 and amplification products corresponding to the nucleotide sequence of SEQ ID NO:2 were obtained. From these results, it was concluded that whether an onion was a tearless onion or a control variety could be discriminated by whether alliinase gene 1 comprising the nucleotide sequence of SEQ ID NO:1 could be detected, and that primers achieving the discrimination could be prepared.

Furthermore, to confirm the versatility of the above-described primers, the effectiveness of the above-described primers was investigated using the genomic DNAs of 14 commercially available onion varieties shown in Table 2, the above-described control variety, and onion #6 as templates. The conditions for PCR were the same as the above-described conditions.

Figure 4:
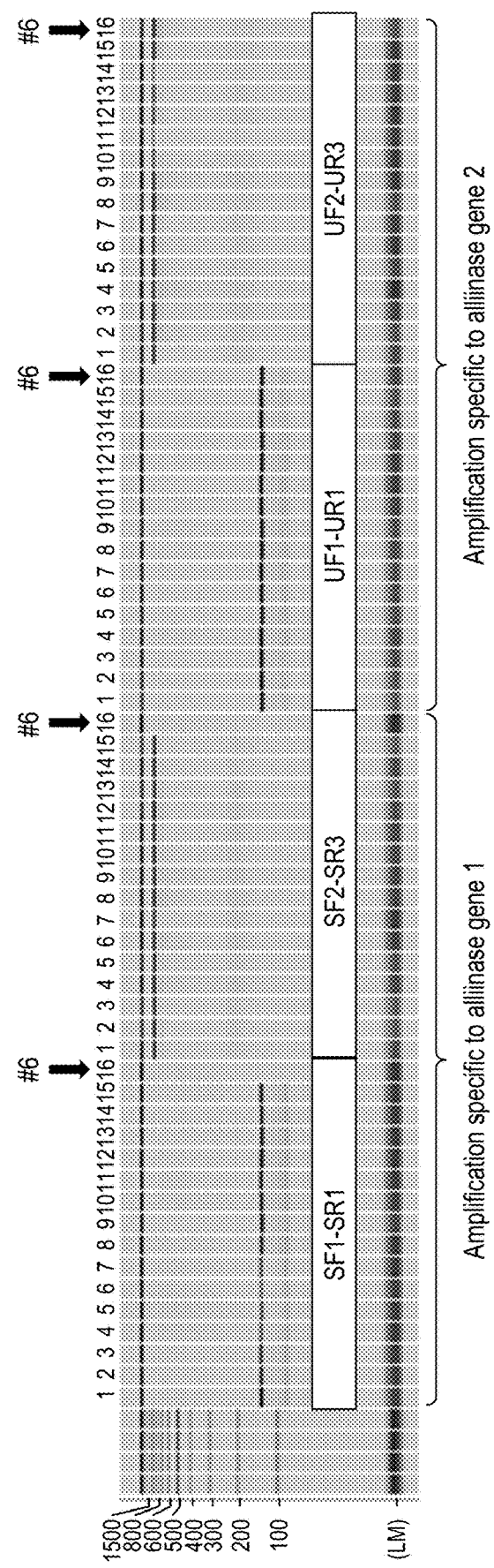
FIG. 4 shows the detection results for alliinase gene 1 and alliinase gene 2 in amplification products of PCR on the genomic DNAs of 14 varieties of commercially available onions, a control variety, and onion #6 as templates using various primer sets.

The results are shown in FIG. 4. The lane numbers in FIG. 4 correspond to the onion variety numbers in Table 3. Lanes 1 to 14 show the analysis results for commercially available varieties, lane 15 is the analysis results for the above-described control variety, and lane 16 is the analysis results for onion #6. The results shown in FIG. 4 confirmed that the 14 commercially available varieties and the control variety had alliinase gene 1 and alliinase gene 2, and that onion #6 had alliinase gene 2 but did not have alliinase gene 1. These results support that the method of determining onion #6 using the above-described primers can be applied widely independently of the variety.

TABLE 2

| Name | | Forward/reverse | 5' → 3' | SEQ ID NO: |
|---|---|---|---|---|
| Alliinase gene 1 specific amplification primers | SF1 | Forward | TGGCAGTAATAAAATGCCAAGCCTT | 5 |
| | SF2 | Forward | ATGCATAATCATGTCTTCATTTGTT | 6 |
| | SF3 | Forward | CAGACATTTCAAAATGGGCGTATCAATACG | 7 |
| | SF4 | Forward | GAGAGGGTTTCGAAGCAGGTAGTCGTTAT | 8 |
| | SR1 | Reverse | ACAGTTTATATTAGCCACTGCTTCT | 9 |
| | SR2 | Reverse | TGTGCTGCTGCCAGTATTCTTCT | 10 |
| | SR3 | Reverse | ATTTGCATCCCTTTATTACTTCATG | 11 |
| | SR4 | Reverse | GTACTTAAATGAAAGGACGGCGGGAGA | 12 |
| Alliinase gene 2 specific amplification primers | UF1 | Forward | TGGCAGTAGTAAAATGCCAAGCCTA | 13 |
| | UF2 | Forward | ATGCATAATCATGTCTTCATTTGTC | 14 |
| | UF3 | Forward | CAGACATTTCAAAATGGACGYATCAACACA | 15 |
| | UF4 | Forward | GAGAGGGTTTCGAAGCGGGCAGTCGTTAC | 16 |
| | UR1 | Reverse | ACAGTTTATATTGGCCACTGCCTCC | 17 |
| | UR2 | Reverse | GGTGGTGCTGCCAATATTCCTCA | 18 |
| | UR3 | Reverse | ATGGATTTGCATCCCTTGATTACTTCCTT | 19 |
| | UR4 | Reverse | GTACTTAAATGAAAGGACGGCGGGATG | 20 |
| Common primers | F3 | Forward | ATATGGTTTACTACTGGCCTCATTACAC | 21 |
| | R3 | Reverse | CCATTCACACTTCACCCATGCATAAG | 22 |

TABLE 3

| No | Region of production | Type |
|---|---|---|
| 1 | Saga | Short-day |
| 2 | Kagoshima | Short-day |
| 3 | New Zealand | Long-day |
| 4 | Shizuoka | Short-day |
| 5 | Kumamoto | Short-day |
| 6 | Nagasaki | Short-day |

TABLE 3-continued

| No | Region of production | Type |
|----|---------------------|------|
| 7  | Awaji    | Intermediate-day |
| 8  | Hokkaido | Long-day_red onion |
| 9  | Chiba    | Short-day |
| 10 | Italy    | Long-day_red onion |
| 11 | Hokkaido | Short-day_ white onion |
| 12 | Hokkaido | Long-day_red onion |
| 13 | Hokkaido | Long-day_ functional onion |
| 14 | Hokkaido | Long-day |
| 15 | Hokkaido | Long-day(control) |
| 16 | Hokkaido | #6 |

Example 4: Use of the Discrimination Method

The above-described primers can be used to select a tearless and non-pungent onion which is incorporated with useful traits from progenies obtained by crossing the tearless and non-pungent onion #6 and a second onion having the useful traits by a common crossing method.

Figure 5:
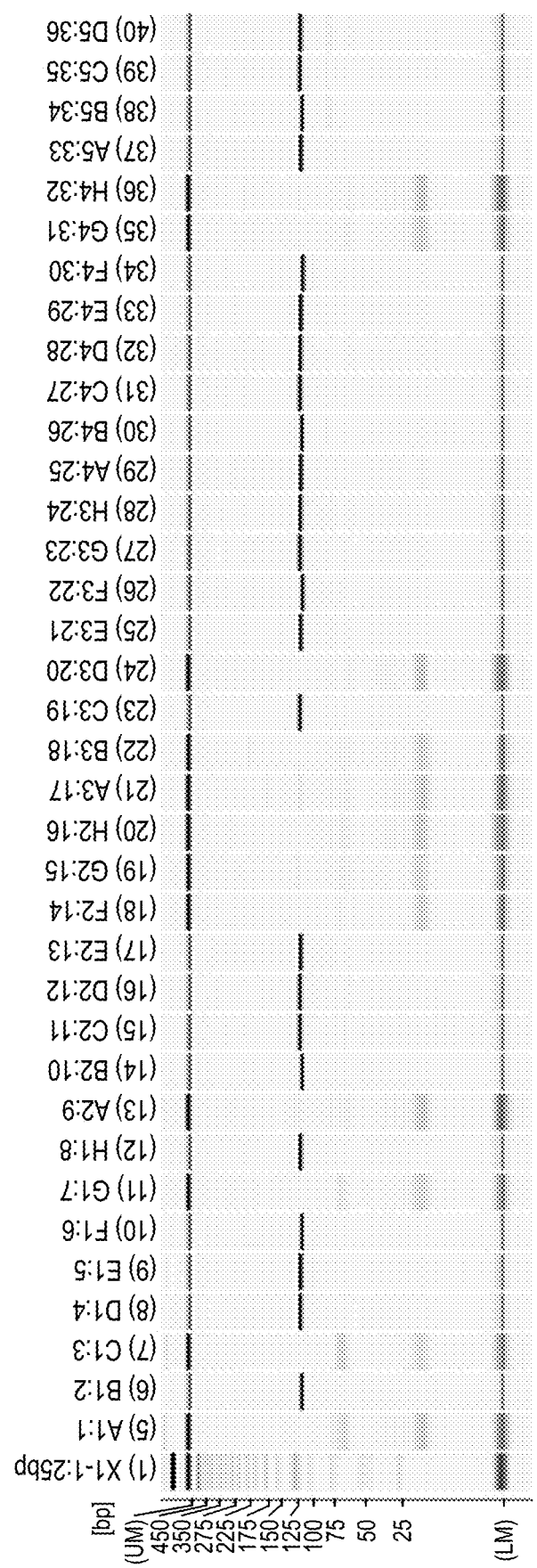
FIG. 5 shows the detection results for alliinase gene 1 in amplification products of PCR on the genomic DNAs of leaves of a plurality of F2 onions derived from onion #6 with no pungent taste as templates using SF2-SR1 as a primer set.

A long-day onion having a good bulb size was crossed with onion #6. Specifically, onion #6 and a male sterile long-day onion having a trait of a good bulb size (HTA that is not a commercially available variety) were crossed by a conventional method in Hokkaido to obtain F1 seeds. The F1 seeds were seeded, and bulbs of the F1 onions (F1 bulbs) were harvested by the conventional planting method in Hokkaido. The harvested F1 bulbs were self-reproduced and cultivated to obtain F2 seeds. The obtained F2 seeds were cultivated by the conventional method to obtain bulbs of the F2 onions (F2 bulbs). Onion selection was performed by sampling leaves of 4249 bulbs in the process of cultivating the F2 bulbs, extracting genomic DNAs, and performing PCR using the genomic DNAs as templates and three primer sets of SF2-SR1, SF1-SR1, and UF2-UR1 among the above-described primers. Then, F2 bulbs were selected for which amplification products corresponding to alliinase gene 2 were obtained, and amplification products corresponding to alliinase gene 1 were not obtained. The F2 bulbs selected according to this criterion are presumed to be tearless and non-pungent onion bulbs. As a result, 866 onion bulbs were selected from 4249 bulbs. FIG. 5 shows one example of the detection results for the amplification products of PCR using genomic DNAs from leaves of a plurality of F2 onions as templates and SF2-SR1 as a primer set. The upper column of FIG. 5 shows the names of the F2 onion samples.

Figure 6:
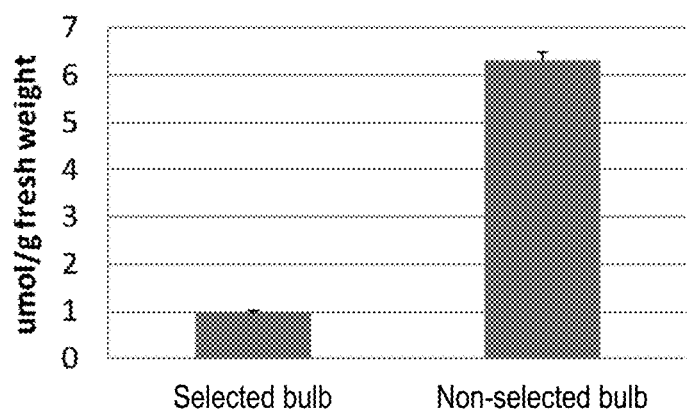
FIG. 6 shows the measurement results for the quantity of pyruvic acid produced in onion bulbs in which alliinase gene 1 was detected in the genomic DNA (selected bulbs) and onion bulbs in which alliinase gene 1 was not detected (non-selected bulbs), among F2 onions derived from onion #6 with no pungent taste.

To confirm the identity between the selection results by PCR and the phenotypes, sensory evaluation was performed, and the quantity of pyruvic acid, which is an indicator of a tear-inducing property and a pungent taste, was measured for 94 F2 bulbs of the F2 onions for which the amplification product of alliinase gene 2 was obtained in the above-described detection, and the amplification product of alliinase gene 1 was not obtained (referred to as "selected bulbs") and for 30 F2 bulbs of the F2 onions for which both the amplification products were obtained (referred to as "non-selected bulbs"). The quantity of pyruvic acid produced was measured using the method disclosed in Patent Literature 1. The measurement results for the quantity of pyruvic acid produced are shown in FIG. 6. The results of sensory evaluation showed that a tear-inducing property and a pungent taste were not sensed in any of the selected bulbs. Additionally, the quantity of pyruvic acid produced in the selected bulbs was approximately 1 μmol/g, which was comparable with the quantity of pyruvic acid produced in the tearless and non-pungent onion disclosed in JP Patent No. 5671657. However, a tear-inducing property and a pungent taste were sensed in the non-selected bulbs in sensory evaluation, and the quantity of pyruvic acid produced were more than 6 μmol/g.

The above results support that the discrimination method of the present invention can accurately select traits of not inducing tears and having no pungent taste.

INDUSTRIAL APPLICABILITY

The present invention can be used to discriminate an onion with no pungent taste in the fields such as agriculture and food manufacturing.

All publications, patents, and patent applications cited in this specification are incorporated fully herein by reference.

The present invention has been explained in detail, but it will become apparent to those skilled in the art that various modifications can be made without departing from the scope of the present invention, and the present invention is not limited to the description in this specification.

The invention claimed is:

1. A method of detecting presence of a first alliinase nucleotide sequence and presence of a second alliinase nucleotide sequence in a nucleic acid derived from an onion, comprising:
 a first detecting step of detecting presence of the first alliinase nucleotide sequence consisting of SEQ ID NO:1 in a nucleic acid derived from the onion; and
 a second detecting step of detecting presence of the second alliinase nucleotide sequence consisting of SEQ ID NO:2 in the nucleic acid derived from the onion.

2. The method according to claim 1, further comprising: detecting whether the onion has:
 a) production of pyruvic acid at disruption of onion cells is reduced compared with conventional varieties;
 b) a quantity of trans-1-propenyl cysteine sulfoxide (PRENCSO) remaining after disruption of onion cells is greater compared with conventional varieties; and
 c) production of lachrymatory factor (LF) at disruption of onion cells is reduced compared with conventional varieties.

3. The method according to claim 1, further comprising: detecting whether production of pyruvic acid at disruption of onion cells is reduced in the onion compared with conventional varieties.

4. The method according to claim 1, further comprising: detecting whether a quantity of trans-1-propenyl cysteine sulfoxide (PRENCSO) remaining after disruption of onion cells that is greater in the onion compared with conventional varieties.

5. The method according to claim 1, further comprising: detecting whether production of lachrymatory factor (LF) at disruption of onion cells is reduced in the onion compared with conventional varieties.

* * * * *

SEQUENCE LISTING

```
<160> NUMBER OF SEQ ID NOS: 22

<210> SEQ ID NO 1
<211> LENGTH: 1663
<212> TYPE: DNA
<213> ORGANISM: Allium cepa

<400> SEQUENCE: 1
ccgagattac aagtggagca ttaaatatcc atagcagagc taattagcta tggagtctta      60
ccacaaagtt ggcagtaata aaatgccaag ccttcttatt ttgatatgca taatcatgtc     120
ttcatttgtt aacaataata tagctcaagc gaaggtgaca tggagtttga aggcagcaga     180
agaggcagaa gcagtggcta atataaactg ttcagggcat gggagagctt ttttggacgg     240
aattctttca gatggatctc ctaaatgcga gtgcaatact tgctacactg gtgcagactg     300
ctctgaaaag attacaggtt gctctgctga tgttgccagt ggtgatggac tgtttctaga     360
agaatactgg cagcagcaca aggaaaacag tgcagtgctg gtttcaggat ggcacagaat     420
```

```
gagctacttt ttcaacccag ttagcaattt catatctttc gagcttgaaa aaacaattaa      480
agaactacat gagatagtcg gaaatgctgc tgcaaaggac aggtacattg tgtttggagt      540
aggggtgact caactcatcc atggattggt catctctctt tcaccaaata tgactgccac      600
tccttgtgca ccacaatcta aagttgttgc tcatgcccct tattatccgg tgtttagaga      660
acaaacaaag tactttgaca agaaagggta cgagtggaaa ggaaatgcag cggattacgt      720
gaacacttca actccagagc aattcattga tggttact tcacctaata acccagaagg        780
tctgcttcgc catgaagtaa taagggatg caaatccatc tacgatatgg tttactactg      840
gcctcattac accccaatca agtacaaagc cgatgaagat atcatgttgt ttacaatgtc      900
taaatacact ggacactctg gtagtcgatt tgggtgggca ctgataaagg atgaaactgt      960
gtataataaa ttgttgaatt acatgacaaa gaacacggag ggcacttccc gagaaacaca     1020
gctacgatcg ctcaaaattc taaagaagt tatagcaatg gttaaaacac agaaaggcac      1080
catgcgcgac ctcaacacat ttggttttca gaaactaaga gagaggtggg taaatatcac     1140
ttcattgctc gataaatccg acagattctc ctatcaaaag cttccacaaa gtgaatattg     1200
caattacttc aggagaatga gacctccatc cccatcttat gcatgggtga agtgtgaatg     1260
ggaagaagac aaagattgct accagacatt tcaaaatggg cgtatcaata cgcaaagtgg     1320
agagggtttc gaagcaggta gtcgttatgt gcgtttgagt ttgatcaaga caaaagatga     1380
ttttgatcaa ctaatgtact atttgaagaa tatggttgaa gcaagagga agactcctct     1440 catcaaacaa cttccaatg atcagatctc ccgccgtcct ttcatttaag tactcatgtt      1500
atgtattgct ctgctgtttt gttagtgtat gactatgttc atacatccta atgctatggt     1560
agtaaggagt atctttctat gcaataaata aagttcatgt ttgtgatcat gtatgggcta     1620
ctatgatttt ataataaaat caattttcat ataaaaaaaa aaa                       1663

<210> SEQ ID NO 2
<211> LENGTH: 1975
<212> TYPE: DNA
<213> ORGANISM: Allium cepa

<400> SEQUENCE: 2
ccacaaagtt ggcagtagta aaatgccaag cctacttatt ttgatatgca taatcatgtc       60
ttcatttgtc aacaataata tagctcaagg gaaggtgaca tggagtttga aggcagcaga      120
agaggcggag gcagtggcca atataaactg ttcagggcat ggaagagctt ttttggatgg      180
aattctttca gatggctctc ctaaatgcga gtgcaatact tgctacactg gtgcagattg      240
ctctcaaaag attacaggtt gctctgcgga tgttgccagg ttaatatttc tctgttcttc      300
acaatacatg gtagtttaac tttatatcaa acacactgga caatatttaa tgacatgctt      360
aaggaattga atgatatatt gtatacacag tgstgatgga ctgwttcttg aggaatattg      420
gcagcascac maggaaaaca gtgcagtgct cgtttcagga tggcacagaa tgagctactt      480
tttcaaccca gytagcaatt tcatatcgtt cgagcttgaa aaaacaatta aggaactaca      540
tgagatagtc ggaaatgctg ctgcaaagga caggtacatt gtgtttggag tcggggtgac      600
tcaactcatc catggattgg tcatctytct ttcaccaaat atgactgcca ctccttgtgc      660
accacaatct aaagttgttg ctcatgcccc tttttatccg gtaactctac gcatgtttct      720
aagttgaact acctagagat aactgttat ttccttatgta ctcgtgtgac tgacttaatt    780
tgaacaaatt aaatgataca ggtgttcaga gaacaaacaa aatatttga caagaaaggg      840
```

```
tacgagtgga aaggaaatgc agcgaattac gtgaacactt caactcctga gcagttcatt    900
gagatggtta cttcacctaa taccccagaa ggtctgcttc gcaaggaagt aatcaaggga    960
tgcaaatcca tttacgatat ggtttactac tggcctcatt acaccccaat caagtacaaa   1020
gccgacgaag atatcatgtt gtttacaatg tctaaataca ctggacactc tggtagtcga   1080
tttgggtatg tccacatatt attacctcac atctttctct acctataatt aacatattta   1140
agttggttag ttagtaactc atactttaat atcttattaa attaggtggg cgttgataaa   1200
ggatgaaacc gtgtataata agttgtwaaa ttacatgaca aaaaacacgg aaggcactcc   1260
tcgggaaaca cagctacgat cgctcaaaat tmtaaaagaa gtcatagcaa tggttaaaac   1320
acagaaaggc accatgcgtg acctcaacac atttggtttt aagaaactaa gagagaggtg   1380
ggtaaatatc actgcattgc tggataaatc agacagattc tcctatcaaa gcttccaca   1440 aagtgaatat tgcaattact tccgaagaat gagacctcca tccccatgta tgtataccag   1500
tatattatca tttattgaaa gatataatat tatagattat aaacataaca atgyagcatt   1560
aatcaatgat atatatatac acgatgacag cttatgcatg ggtgaagtgt gaatgggaag   1620
aagacaaaga ttgctaccag acatttcaaa atggacgyat caacacacaa agtggagagg   1680
gtttcgaagc gggcagtcgt tacgtgcgty tgagtttgat caagacaaag gatgattttg   1740
atcaactcat gtactatttg aagactatgg ttgaagcaaa gaggaagact cctctcatca   1800
aacaactttc caatgatcag acatcccgcc gtcctttcat ttaagtactc atgttatgta   1860
tcgctcgctg ttttgttagt gtatgactat gttcatacat cctaatgcta tggtcgtaag   1920
gagttcctat ctttgtaata aataaagttc atgtttgtga tcatgtatgg rctac        1975
```

```
<210> SEQ ID NO 3
<211> LENGTH: 27
<212> TYPE: DNA
<213> ORGANISM: Artificial
<220> FEATURE:
<223> OTHER INFORMATION: Primer

<400> SEQUENCE: 3
atggagtctt accacaaagt tggcagt                                         27

<210> SEQ ID NO 4
<211> LENGTH: 29
<212> TYPE: DNA
<213> ORGANISM: Artificial
<220> FEATURE:
<223> OTHER INFORMATION: Primer

<400> SEQUENCE: 4
gtagcccata catgatcaca aacatgaac                                       29

<210> SEQ ID NO 5
<211> LENGTH: 25
<212> TYPE: DNA
<213> ORGANISM: Artificial
<220> FEATURE:
<223> OTHER INFORMATION: Primer

<400> SEQUENCE: 5
tggcagtaat aaaatgccaa gcctt                                           25

<210> SEQ ID NO 6
<211> LENGTH: 25
<212> TYPE: DNA
<213> ORGANISM: Artificial
```

<220> FEATURE:
<223> OTHER INFORMATION: Primer

<400> SEQUENCE: 6
atgcataatc atgtcttcat ttgtt                                                 25

<210> SEQ ID NO 7
<211> LENGTH: 30
<212> TYPE: DNA
<213> ORGANISM: Artificial
<220> FEATURE:
<223> OTHER INFORMATION: Primer

<400> SEQUENCE: 7
cagacatttc aaaatgggcg tatcaatacg                                            30

<210> SEQ ID NO 8
<211> LENGTH: 29
<212> TYPE: DNA
<213> ORGANISM: Artificial
<220> FEATURE:
<223> OTHER INFORMATION: Primer

<400> SEQUENCE: 8
gagagggttt cgaagcaggt agtcgttat                                             29

<210> SEQ ID NO 9
<211> LENGTH: 25
<212> TYPE: DNA
<213> ORGANISM: Artificial
<220> FEATURE:
<223> OTHER INFORMATION: Primer

<400> SEQUENCE: 9
acagtttata ttagccactg cttct                                                 25

<210> SEQ ID NO 10
<211> LENGTH: 23
<212> TYPE: DNA
<213> ORGANISM: Artificial
<220> FEATURE:
<223> OTHER INFORMATION: Primer

<400> SEQUENCE: 10
tgtgctgctg ccagtattct tct                                                   23

<210> SEQ ID NO 11
<211> LENGTH: 25
<212> TYPE: DNA
<213> ORGANISM: Artificial
<220> FEATURE:
<223> OTHER INFORMATION: Primer

<400> SEQUENCE: 11
atttgcatcc ctttattact tcatg                                                 25

<210> SEQ ID NO 12
<211> LENGTH: 27
<212> TYPE: DNA
<213> ORGANISM: Artificial
<220> FEATURE:
<223> OTHER INFORMATION: Primer

<400> SEQUENCE: 12
gtacttaaat gaaaggacgg cgggaga                                               27

```
<210> SEQ ID NO 13
<211> LENGTH: 25
<212> TYPE: DNA
<213> ORGANISM: Artificial
<220> FEATURE:
<223> OTHER INFORMATION: Primer

<400> SEQUENCE: 13
tggcagtagt aaaatgccaa gccta                                           25

<210> SEQ ID NO 14
<211> LENGTH: 25
<212> TYPE: DNA
<213> ORGANISM: Artificial
<220> FEATURE:
<223> OTHER INFORMATION: Primer

<400> SEQUENCE: 14
atgcataatc atgtcttcat ttgtc                                           25

<210> SEQ ID NO 15
<211> LENGTH: 30
<212> TYPE: DNA
<213> ORGANISM: Artificial
<220> FEATURE:
<223> OTHER INFORMATION: Primer

<400> SEQUENCE: 15
cagacatttc aaaatggacg yatcaacaca                                      30

<210> SEQ ID NO 16
<211> LENGTH: 29
<212> TYPE: DNA
<213> ORGANISM: Artificial
<220> FEATURE:
<223> OTHER INFORMATION: Primer

<400> SEQUENCE: 16
gagagggttt cgaagcgggcag tcgttac                                       29

<210> SEQ ID NO 17
<211> LENGTH: 25
<212> TYPE: DNA
<213> ORGANISM: Artificial
<220> FEATURE:
<223> OTHER INFORMATION: Primer

<400> SEQUENCE: 17
acagtttata ttggccactg cctcc                                           25

<210> SEQ ID NO 18
<211> LENGTH: 23
<212> TYPE: DNA
<213> ORGANISM: Artificial
<220> FEATURE:
<223> OTHER INFORMATION: Primer

<400> SEQUENCE: 18
ggtggtgctg ccaatattcc tca                                             23

<210> SEQ ID NO 19
<211> LENGTH: 29
<212> TYPE: DNA
<213> ORGANISM: Artificial
<220> FEATURE:
<223> OTHER INFORMATION: Primer
```

```
<400> SEQUENCE: 19
atggatttgc atcccttgat tacttcctt                                              29

<210> SEQ ID NO 20
<211> LENGTH: 27
<212> TYPE: DNA
<213> ORGANISM: Artificial
<220> FEATURE:
<223> OTHER INFORMATION: Primer

<400> SEQUENCE: 20
gtacttaaat gaaaggacgg cgggatg                                                27

<210> SEQ ID NO 21
<211> LENGTH: 28
<212> TYPE: DNA
<213> ORGANISM: Artificial
<220> FEATURE:
<223> OTHER INFORMATION: Primer

<400> SEQUENCE: 21
atatggttta ctactggcct cattacac                                               28

<210> SEQ ID NO 22
<211> LENGTH: 26
<212> TYPE: DNA
<213> ORGANISM: Artificial
<220> FEATURE:
<223> OTHER INFORMATION: Primer

<400> SEQUENCE: 22
ccattcacac ttcacccatg cataag                                                 26
```